United States Patent [19]

Henning et al.

[11] Patent Number: 4,595,685

[45] Date of Patent: Jun. 17, 1986

[54] BENZOTHIAZINE DERIVATIVES

[75] Inventors: Rainer Henning, Hattersheim am Main; Ulrich Lerch, Hofheim am Taunus; Joachim Kaiser, Frankfurt am Main, all of Fed. Rep. of Germany

[73] Assignee: Hoechst Aktiengesellschaft, Fed. Rep. of Germany

[21] Appl. No.: 684,711

[22] Filed: Dec. 21, 1984

[30] Foreign Application Priority Data

Dec. 27, 1983 [DE]  Fed. Rep. of Germany ....... 3347173

[51] Int. Cl.[4] .................. C07D 279/10; C07D 417/12; A61K 31/54
[52] U.S. Cl. ...................................... 514/225; 544/51; 544/52
[58] Field of Search ...................... 544/52, 51; 514/225

[56] References Cited

U.S. PATENT DOCUMENTS 3,622,572 11/1971 Krapcho ............................. 544/52
3,711,478 1/1973 Irmscher et al. ..................... 544/52
3,733,321 5/1973 Krapcho ............................. 544/52

FOREIGN PATENT DOCUMENTS 116368 8/1984 European Pat. Off. ............. 544/52
1545702 7/1969 Fed. Rep. of Germany .
1304588 1/1973 United Kingdom .

OTHER PUBLICATIONS

Prasad, J. Med. Chem. 12, pp. 290–294 (1969).
Mannhold et al., Pharmazie heute, vol. 3, pp. 139–146 (1983).

Primary Examiner—John M. Ford
Attorney, Agent, or Firm—Finnegan, Henderson, Farabow, Garrett & Dunner

[57] ABSTRACT

Benzothiazine derivatives of the formula I

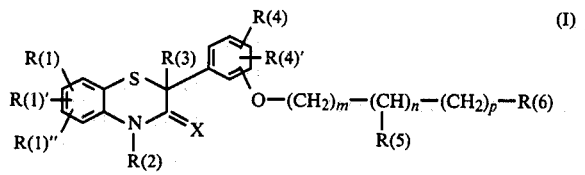

with (R(1), R(1)', R(1)'', R(4) and R(4)' equal to hydrogen, alkyl, alkoxy, halogen, nitro, hydroxyl, acetamido or amino; R(2) equal to hydrogen, alkyl, alkenyl, phenyl; R(3) equal to hydrogen, alkyl, alkenyl, phenyl; R(5) equal to hydrogen or ($C_1$–$C_3$)-alkyl; R(6) equal to one of the following groups,

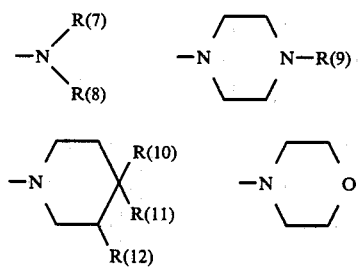

with R(7) and R(8) equal to hydrogen, alkyl, cycloalkyl, phenyl; R(9) equal to hydrogen, alkyl, phenyl, pyridyl, pyrimidinyl or benzoyl; R(10) equal to hydrogen, alkyl, phenyl; R(11) equal to hydrogen, hydroxyl, alkoxy or, together with R(12), a bond; and R(12) equal to hydrogen or, together with R(11), a bond; m equal to 1, 2, 3 or 4; n equal to 0 or 1; p equal to 0, 1, 2, 3 or 4, and X equal to oxygen or two hydrogen atoms, and salts of the compounds of the formula I with physiologically tolerated acids and a process for the preparation of compounds I, likewise a method of treatment of disturbances of the calcium balance of a human body are described.

12 Claims, No Drawings

BENZOTHIAZINE DERIVATIVES

It is known that compounds which prevent the influx of calcium ions into cells can be used as therapeutic agents for the treatment of various diseases, in particular of the cardiovascular system in humans and other warm-blooded species (see, for example, R. A. Janis and D. J. Triggle, J. Med. Chem. 26, 775 (1983)). 2-Methylene-2,3-dihydro-3-oxo-1,4-benzothiazine 1,1-dioxide compounds are described in German Offenlegungsschrift 2,912,445 to be used for controlling cardiovascular disorders, in particular cardiac arrhythmias.

British Pat. No. 1,374,283 describes benzothiazine derivatives having tranquillizing, antidepressant and antibacterial effects.

British Pat. No. 1,388,054 describes antiinflammatory agents having the benzothiazine structure; similar compounds are also found in J. Med. Chem. 12 (1969) 290–294.

In British Pat. No. 1,373,537 are found aminoalkylbenzylidene-2H-benzothiazin-3(4H)-ones and related compounds having antidepressant effects.

Substituted 2-phenyl-1,4-benzothiazin-3(4H)-ones are mentioned as inhibitors of 1,4-dipyrrolidino-2-butine in J. Med. Chem. 6 (1963) 214–216.

Finally, 1,4-benzothiazine derivatives having potential antihypertensive effects are described in J. Med. Chem. 16 (1973) 776–779.

However, no benzothiazine derivatives having a calcium-antagonistic effect have hitherto been disclosed.

The present invention relates to benzothiazine derivatives of the formula I, which have such an effect,

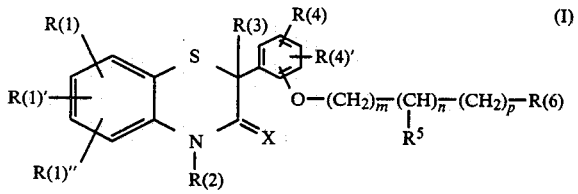

and in which R(1), R(1)' and R(1)'' are identical or different and are independent of one another, and denote hydrogen, $(C_1-C_4)$-alkyl, $(C_1-C_3)$-alkoxy, halogen, nitro, hydroxyl, acetamido or amino, R(2) denotes hydrogen, $(C_1-C_{10})$-alkyl, straight-chain or branched, $(C_3-C_{10})$-alkenyl, straight-chain or branched, phenyl which can optionally be substituted by one, two or three substituents from the group comprising $(C_1-C_4)$-alkyl, $(C_1-C_3)$-alkoxy, halogen, $(C_1-C_2)$-alkylenedioxy alkylenedioxy or nitro, phenyl-$(C_1-C_4)$-alkyl, it being possible for the phenyl ring to be substituted by one, two or three substituents from the group comprising $(C_1-C_4)$-alkyl, $(C_1-C_3)$-alkoxy, halogen, $(C_1-C_2)$-alkylenedioxy or nitro, $(C_4-C_8)$-cycloalkyl-$(C_1-C_4)$-alkyl, or $(C_4-C_8)$-cycloalkyl, R(3) denotes hydrogen, $(C_1-C_{10})$-alkyl, straight-chain or branched, $(C_3-C_{10})$-alkenyl, straight-chain or branched, phenyl-$(C_1-C_4)$-alkyl, it being possible for the phenyl radical to be substituted by one, two or three substituents from the group comprising $(C_1-C4)$-alkyl, $(C_1-C3)$alkoxy, halogen, $(C_1-C_2)$-alkylenedioxy or nitro, $(C_4-C_8)$-cycloalkyl, or $(C_4-C_8)$-cycloalkyl-$(C_1-C_4)$-alkyl, R(4) and R(4)' are identical or different and, independently of one another, denote hydrogen, $(C_1-C_4)$-alkyl, $(C_1-C_3)$-alkoxy, halogen, nitro, hydroxyl, acetamido or amino, R(5) denotes hydrogen or $(C_1-C_3)$-alkyl, R(6) denotes a part structure from the following group,

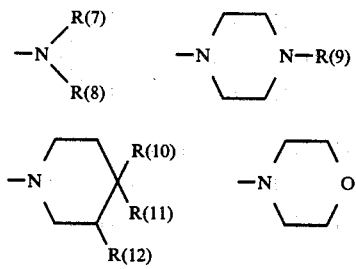

in which R(7) and R(8) are identical or different and, independently of one another, denote hydrogen, $(C_1-C_{10})$-alkyl, $(C_4-C_8)$-cycloalkyl, $(C_4-C_8)$-cycloalkyl-$(C_1-C_4)$-alkyl, phenyl-$(C_1-C_6)$-alkyl, it being possible for the phenyl radical to be substituted by one, two or three radicals from the group comprising $(C_1-C_4)$-alkyl, $(C_1-C_4)$-alkoxy, $(C_1-C_2)$-alkylenedioxy, halogen or hydroxyl, or pyridyl-$(C_1-C_4)$-alkyl, R(9) denotes hydrogen, $(C_1-C_{10})$-alkyl, straight-chain or branched, phenyl, it being possible for the phenyl radical to be substituted by one, two or three radicals from the group comprising $(C_1-C_4)$-alkyl, $(C_1-C_4)$-alkoxy, $(C_1-C_2)$-alkylenedioxy, halogen or hydroxyl, phenyl$(C_1-C_4)$-alkyl, it being possible for the phenyl radical to be substituted by one, two or three radicals from the group comprising $(C_1-C_4)$-alkyl, $(C_1-C_4)$-alkoxy, $(C_1-C_2)$-alkylenedioxy, halogen or hydroxyl, pyridyl, pyrimidinyl, $(C_1-C_5)$-alkanoyl, phenyl-$(C_1-C_4)$-alkanoyl, or benzoyl, it being possible for the phenyl radical in each case to be substituted by one, two or three radicals from the group comprising $(C_1-C_4)$-alkyl, $(C_1-C_4)$-alkoxy, $(C_1-C_2)$-alkylenedioxy, halogen or hydroxyl, R(10) denote hydrogen, $(C_1-C_{10})$-alkyl, phenyl, it being possible for the phenyl radical to be substituted by one, two or three radicals from the group comprising $(C_1-C_4)$-alkyl, $(C_1-C_4)$-alkoxy, $(C_1-C_2)$-alkylenedioxy, halogen or hydroxyl, or phenyl-$(C_1-C_4)$-alkyl, it being possible for the phenyl radical to be substituted by one, two or three radicals from the group comprising $(C_1-C_4)$-alkyl, $(C_1-C_4)$-alkoxy, $(C_1-C_2)$-alkylenedioxy, halogen or hydroxyl, R(11) denotes hydrogen, hydroxyl, $(C_1-C_4)$-alkoxy or, together with R(12), denotes a bond, and R(12) denotes hydrogen or, together with R(11), denotes a bond;

in which formula I in addition m denotes 1, 2, 3 or 4, n denotes 0 or 1, p denotes 0, 1, 2, 3 or 4, and X denotes oxygen or two hydrogen atoms, as well as the salts of the compounds of the formula I with physiologically tolerated acids.

Preferred compounds of the formula I are those in which

R(1) and R(1)' are identical or different and, independently of one another, denote hydrogen, methyl, ethyl, methoxy, ethoxy, chlorine, bromine, nitro or acetamido, R(1)" denotes hydrogen, R(2) denotes hydrogen, $(C_1-C_6)$-alkyl, straight-chain or branched, benzyl, phenethyl, allyl, phenyl, 4-methoxyphenyl, 3-methoxyphenyl, 3,4-methylenedioxyphenyl, 3,4,5-trimethoxyphenyl, 3,4-dimethoxyphenyl, cyclohexylmethyl, cyclopentyl, cyclohexyl, cycloheptyl, 4-methoxybenzyl, 3,4-dimethoxybenzyl, 3,4,5-trimethoxybenzyl or 3,4-methylenedioxybenzyl, R(3) denotes hydrogen, $(C_1-C_6)$-alkyl, straight-chain or branched, benzyl, phenylethyl, allyl, cyclopentyl or cyclohexyl, R(4) denotes hydrogen, methyl, methoxy, ethoxy, chlorine, nitro, hydroxyl, acetamido or amino, R(4)' denotes hydrogen, R(5) denotes hydrogen or methyl, R(6) denotes a part structure from the following group,

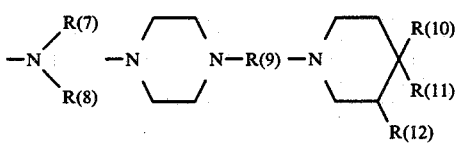

in which R(7) denotes hydrogen, methyl, ethyl, propyl or isopropyl, R(8) denotes hydrogen, methyl, ethyl, propyl, isopropyl, cyclopentylethyl, cyclohexylethyl, phenyl-$(C_1-C_4)$-alkyl, it being possible for the phenyl radical to be substituted by one, two or three radicals from the group comprising $(C_1-C_4)$-alkyl, $(C_1-C_4)$-alkoxy, $(C_1-C_2)$-alkylenedioxy, halogen or hydroxyl, or pyridyl-$(C_1-C_4)$-alkyl, R(9) is defined as indicated above, R(10) denotes phenyl which can optionally be substituted by one, two or three radicals from the group comprising $(C_1-C_4)$-alkyl, $(C_1-C_4)$-alkoxy, $(C_1-C_2)$-alkylenedioxy, halogen or hydroxyl, or phenyl-$(C_1-C_4)$-alkyl, it being possible for the phenyl radical to be substituted by one, two or three radicals from the group comprising $(C_1-C_4)$-alkyl, $(C_1-C_4)$-alkoxy, $(C_1-C_2)$-alkylenedioxy, halogen or hydroxyl, R(11) denotes hydrogen and hydroxyl, methoxy or, together with R(12), denotes a bond, R(12) denotes hydrogen or, together with R(11), denotes a bond;

in which formula I in addition
m denotes 1, 2 or 3,
n denotes 0 or 1,
p denotes 1, 2 or 3, and
X denotes oxygen or two hydrogen atoms, as well as the salts of these compounds of the formula I with physiologically tolerated acids.

Particularly preferred compounds of the formula I are those in which

R(1) denotes hydrogen, methyl, methoxy, fluorine or chlorine,

R(1)' and R(1)" denote hydrogen,

R(2) denotes hydrogen, methyl, ethyl, propyl, isopropyl, butyl, sec.-butyl, isobutyl, benzyl, phenethyl, 4-methoxyphenyl, 3-methoxyphenyl, 3,4-dimethoxyphenyl, 3,4,5-trimethoxyphenyl, cyclohexylmethyl, cyclopentyl, cyclohexyl, cycloheptyl, 4-methoxybenzyl, 3,4-dimethoxybenzyl, 3,4,5-trimethoxybenzyl or 3,4-methylenedioxybenzyl, R(3) denotes hydrogen, methyl, ethyl, propyl, isopropyl, butyl, sec.-butyl, isobutyl, benzyl, phenylethyl, allyl, cyclopentyl or cyclohexyl, R(4) denotes hydrogen, methoxy, methyl, chlorine, nitro or hydroxyl, R(4)' denotes hydrogen, R(5) denotes hydrogen, R(6) denotes a part structure from the following group,

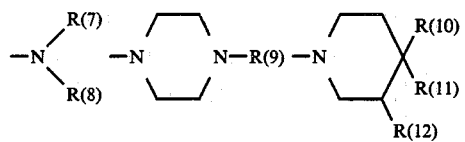

in which R(7) denotes hydrogen or methyl, R(8) denotes phenyl-$(C_1-C_4)$-alkyl, it being possible for the phenyl radical to be substituted by one, two or three radicals from the group comprising methyl, methoxy, chlorine, methylenedioxy or hydroxyl, R(9) is defined as above, R(10) denotes phenyl, it being possible for the phenyl radical to be substituted by one, two or three radicals from the group comprising methyl, methoxy, chlorine, methylenedioxy or hydroxyl, R(11) denotes hydrogen, hydroxyl, methoxy or, together with R(12), denotes a bond, and R(12) denotes hydrogen or, together with R(11), denotes a bond;

in which formula I in addition
m denotes 1, 2 or 3,
n denotes 0,
p denotes 0, 1 or 2, and
X denotes oxygen, as well as the salts of these compounds of the formula I with physiologically tolerated acids.

Suitable acids of this type are inorganic acids, such as hydrochloric acid, hydrobromic acid, hydriodic acid, sulfuric acid, phosphoric acid or nitric acid, or organic acids, such as tartaric acid, malic acid, lactic acid, maleic acid, fumaric acid, malonic acid, oxalic acid, gluconic acid, camphorsulfonic acid, benzenesulfonic acid, acetic acid, propionic acid or p-toluenesulfonic acid.

Especially preferred compounds of the formula I as defined above are those in which R(2) is hydrogen, methyl, ethyl, propyl, isopropyl or phenyl, R(3) is methyl, ethyl, propyl, isopropyl, butyl, sec-butyl, isobutyl, cyclopentyl or cyclohexyl, R(4) is hydrogen, methoxy, methyl or chlorine, R(6) is a part structure from the following group

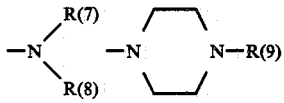

in which R(7) is methyl, R(8) is defined as indicated above, R(9) is phenyl-$(C_1-C_4)$-alkyl, it being possible for the phenyl radical to be substituted by one, two or three radicals from the group comprising $(C_1-C_2)$-alkoxy, $(C_1-C_2)$-alkylenedioxy or hydroxyl, m is 3,
p is 0 or 1,
and their physiologically tolerated salts.

Unless otherwise indicated, halogen denotes fluorine or chlorine.

The compounds of the formula I have asymmetric carbon atoms and can thus occur as enantiomers or diastereomers. The invention relates both to the pure isomers and to their mixtures. Mixtures of diastereomers can be separated into the components by conventional methods, for example selective crystallization from suitable solvents or chromatography on silica gel or aluminum oxide. Racemates can likewise be resolved into the individual enantiomers by customary methods, thus, for example, by salt formation with optically active acids, such as camphorsulfonic acid or dibenzoyltartaric acid, and selective crystallization, or by derivatization with suitable optically active reagents, separation of the diastereomeric derivatives, and cleavage again.

The invention also relates to a process for the preparation of compounds of the formula I, which comprises
(a) reacting a compound of the formula II

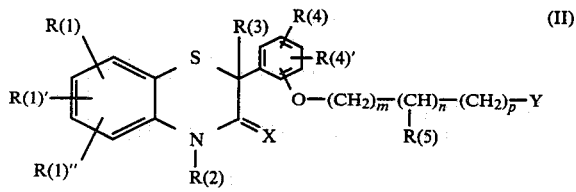

in which R(1), R(1)', R(1)", R(2), R(3), R(4), R(4)', R(5), X, m, n and p have the same meaning as in formula I, and in which Y denotes a leaving group which can undergo nucleophilic displacement, in particular a halogen atom, a sulfonic acid radical, preferably a methanesulfonyl radical, a benzenesulfonyl radical, a toluenesulfonyl radical or a trifluoromethanesulfonyl radical, with one of the compounds of the formulae IIIa, IIIb, IIIc or IIId,

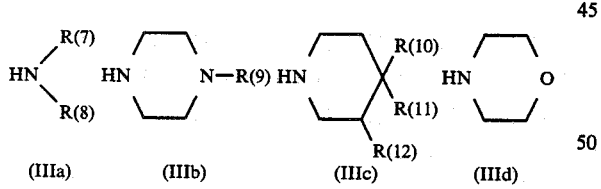

in which R(7), R(8), R(9), R(10), R(11) and R(12) have the same meaning as in formula I, under the conditions of nucleophilic substitution, preferably in a polar organic solvent, such as an alcohol, preferably methanol, ethanol, propanol or isopropanol, or a lower ketone, preferably acetone or methyl ethyl ketone, or dimethylformamide, dimethyl sulfoxide or sulfolane, or a hydrocarbon, preferably toluene, with or without the presence of an auxiliary base to capture the acid which is formed, preferably in the presence of potassium carbonate, sodium carbonate, triethylamine, N-ethylmorpholine or pyridine, at a temperature between 0° and 160° C., preferably between 20° and 120° C., or which comprises
(b) reacting a compound of the formula IV

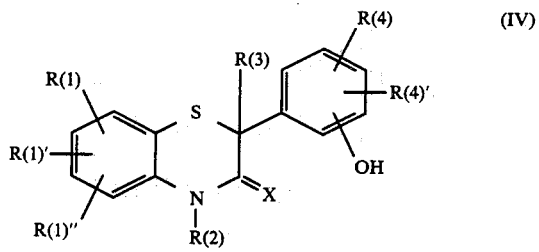

in which R(1), R(1)', R(1)", R(2), R(3), R(4), R(4)' and X have the same meaning as in formula I, with a compound of the formula V

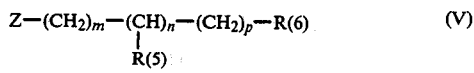

in which Z is defined identically to Y in formula II, and in which R(5), R(6), R(7), R(8), R(9), R(10), R(11), R(12), m, n and p have the same meaning as in formula I, either in a polar aprotic solvent, such as dimethylformamide, dimethyl sulfoxide, tetrahydrofuran, sulfolane or N-methylpyrrolidone, in the presence of a strong base, such as sodium hydride, potassium hydride, sodamide, lithium diisopropylamide, butyllithium or lithium hexamethyldisilazide, at a temperature between −40° and +60° C., preferably between −10° and −30° C., or in a protic or aprotic polar organic solvent, such as a lower alcohol, for example methanol, ethanol or isopropanol, or a lower ketone, preferably acetone or methyl ethyl ketone, or in dimethylformamide, in the presence of a weak to moderately strong base, such as an alkali metal or alkaline earth metal hydroxide or carbonate or an amide such as, for example, triethylamine, N-ethylmorpholine, N-methyldiisopropylamine or pyridine, at a temperature between 0° and 160° C. preferably between 20° and 120° C.

Compounds of the formula II, which are likewise new and to which the invention relates, are obtained from substituted aminothiophenols of the formula VI

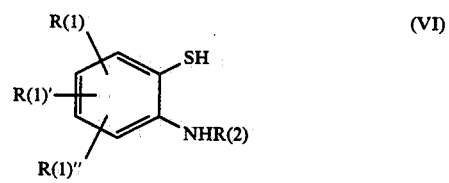

in which R(1), R(1)' and R(1)" have the same meaning as in formula I, by reaction with a compound of the formula

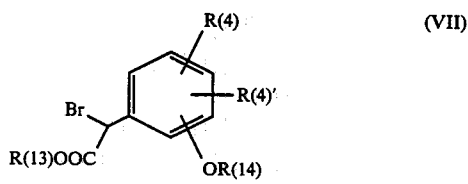

n which R(4) and R(4)' have the same meaning as in formula I, and in which R(13) represents a lower alkyl radical, and R(14) represents a protective group which can be eliminated under mild conditions, such as, for example, a methyl, benzyl or acetyl group, without solvent or in a polar organic solvent, such as, for example, dimethylformamide, at 0° to 60° C., compounds of the formula VIII being obtained (in analogy to Ber. Dt. Chem. Ges. 30, 2389 (1897)), and

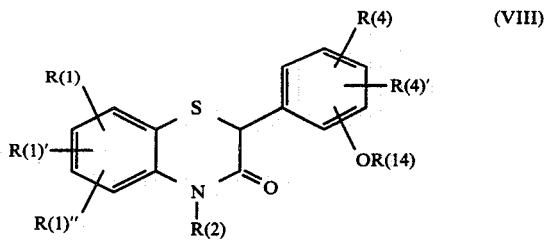

subsequent elimination of the protective group R(14) under suitable conditions, thus, for example, by catalytic hydrogenation for the benzyl group, reaction with boron tribromide, trimethyliodosilane or pyridine hydroboron chloride for the methyl group, or potassium carbonate in alcoholic solution for the acetyl group.

When compounds of the formula VI with R(2)=H are used, radicals R(2) which do not denote H can be introduced into the compounds of the formula VIII by alkylation in the presence of a base, such as, for example, potassium carbonate, or by arylation with a halogenated aromatic compound in the presence of a copper catalyst.

Radicals R(3) can be introduced into compounds of the formula VIII by alkylation with an alkyl halide in the presence of a strong base, such as sodium hydride or a lithium amide. When starting from compounds of the formula VIII with R(2)=H, this results in compounds of the formula VIIIa with R(2)=R(3).

When compounds of the formula VIII with R(2)≠H are used, it is also possible to obtain compounds of the formula VIIIa with R(2)≠R(3).

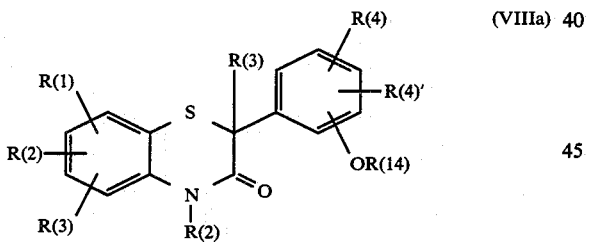

The compounds of the formula IV thus obtained, in which X denotes an oxygen atom, can be converted into compounds of the formula IV in which X denotes two hydrogen atoms by reduction with an aluminum hydride or diborane. This reduction can also be carried out at the stage of the compounds of the formula VIII.

The compounds of the formula IV can subsequently be reacted, under the conditions described for process variant (b), with a compound of the formula IX

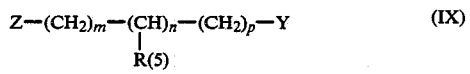

in which R(5), m, n and p have the same meaning as in formula I, Y has the same meaning as in formula II, and Z denotes a leaving group which can be identical to or different from Y and otherwise has the same meaning as Y, to give the compounds of the formula II.

Compounds of the formula V are obtained in a manner known per se from compounds of the formulae IIIa, IIIb, IIIc or IIId by reaction with compounds of the formula IX under the conditions described for process variant (a).

Some compounds of the formula VII are known from the literature (see, for example, J. Med. Chem. 16, 1043 (1973)) or are obtained in an analogous manner, by reaction with phosphorus tribromide, from the corresponding substituted mandelic esters of the formula X

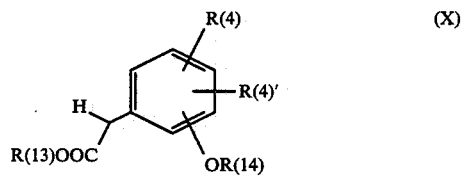

which are obtained from the corresponding benzaldehydes of the formula XI via the cyanohydrins in analogy to Arch Pharm. 308, 338 (1975).

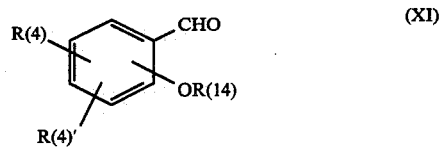

The compounds of the formula I, according to the invention, exhibit pharmacological and biochemical effects, in particular calcium-antagonistic effects, and can thus be used for the treatment of all pathological states which derive from disturbance of the calcium balance of a warm-blooded animal.

Their calcium-antagonistic efficacy can be shown by the biochemical test model of displacement of tritium-labeled nitrendipine. This involves membrane preparations which contain isolated calcium channels being loaded with the labeled substance. After incubation with the test substance, the liberated radioactivity in the supernatant is determined. In this model, the compounds of the formula I, according to the invention, have $IC_{50}$ values of $10^{-6}$ molar to $10^{-10}$ molar. The best of the compounds are inferior in their action only to compounds having the dihydropyridine structure. The compounds of the formula I are likewise very effective in other test models with which a calcium-antagonistic effect can be demonstrated, for example the coronary blood flow in the isolated guinea pig heart or the action potential of the isolated guinea pig papillary muscle.

The compounds of the formula I, according to the invention, and their pharmacologically tolerated salts diminish the influx of calcium ions into cells and are thus suitable for the treatment of the cardiovascular system in the case of appropriate complaints, for example for various forms of angina pectoris, tachycardia, cardiac arrythmias and high blood pressure. They are effective within a wide dose range. The level of the dose administered depends on the type of treatment desired, on the mode of administration, on the condition, type and size of the mammal treated. On oral administration, satisfactory results are achieved with doses of 0.01 to 100 mg, preferably 0.1 to 20 mg, in particular 0.5-15 mg, of a compound of the formula I per kg body weight. In humans, the daily dose varies between 10 and 800 mg, preferably 20 to 500 mg, it being possible to administer single doses of 5 to 200 mg, in particular 5–100 mg, preferably once to three times a day.

The dose for intravenous and intramuscular administration is 1 to 300 mg, preferably 5 to 150 mg, each day.

The pharmacologically utilizable compounds of the present invention, and their salts, can be used for the preparation of pharmaceutical products which contain an effective amount of the active substance, together with vehicles, and which are suitable for enteral and parenteral administration. Tablets or gelatin capsules which contain the active compound together with diluents, for example lactose, dextrose, sucrose, mannitol, sorbitol, cellulose and/or glycine, and lubricants, such as diatomaceous earth, talc, stearic acid or its salts, such as magnesium or calcium stearate, and/or polyethylene glycol, are preferably used. Tablets also contain binders, such as magnesium aluminum silicate, starch, gelatin, tragacanth, methylcellulose, sodium carboxymethylcellulose and/or polyvinylpyrrolidone and, where necessary, colorants, flavorings and sweeteners. Injectable solutions are preferably isotonic aqueous solutions or suspensions which can be sterilized and can contain auxiliaries, such as preservatives, stabilizers, wetting and/or emulsifying agents, solubilizers, salts to regulate the osmotic pressure, and/or buffer substances. The pharmaceutical products according to the invention, which, if desired, can contain other pharmacologically valuable substances, are prepared by, for example, conventional mixing, granulating and coating processes, and contain 0.1% to about 75%, preferably about 1% to about 50%, of the active compound.

The examples which follow below are intended to illustrate the invention without restricting it to these examples.

EXAMPLE 1

2,3-Dihydro-2,4-dimethyl-2-[[2-[4-[N-[2-(3,4-dimethoxyphenyl)ethyl]-N-methyl]amino]butoxy]phenyl]benzothiazin-3-one hydrochloride (a) Methyl 2-methoxymandelate 65.1 g (1 mole) of potassium cyanide and 129.3 g of 2-methoxybenzaldehyde are mixed with 775 ml of dry diethyl ether. While cooling well and stirring vigorously, 500 ml of 2N HCl are added dropwise. The ether phase is separated off, and 332.5 ml of methanol are added. HCl gas is passed in until the solution is saturated. The resulting precipitate is filtered off with suction, washed with ether and dissolved in 600 ml of water. The resulting oil is extracted with ether, and the ether phase is dried with $Na_2SO_4$ and concentrated. 109.7 g of colorless oil are obtained.

(b) Methyl 2-bromo-2-(2-methoxyphenyl)acetate 146.6 ml (1.57 moles) of phosphorus tribromide are added dropwise to 109.7 g (0.562 mole) of methyl 2-methoxymandelate, while cooling well. After 3 hours stirring at room temperature, the mixture is poured into 3N NaCl solution, and extracted with methylene chloride. After washing the organic phase with water, it is dried with $Na_2SO_4$ and is concentrated. 140.7 g of the title compound are obtained as a yellowish oil which is used further without purification.

$^1$H-NMR(CDCl$_3$): δ=7.5–6.7 (m,4H); 5.8 (s,1H); 3.75 (s,3H); 3.67 (s,3H) ppm.

(c) 2,3-Dihydro-2-(2-methoxyphenyl)benzothiazin-3-one 50 g of methyl 2-bromo-2-(2-methoxyphenyl)acetate are dissolved in 200 ml of dry dimethylformamide. While stirring and cooling, 24 ml (0.1929 mole) of o-aminothiophenol are added dropwise. After warming to room temperature, the mixture is stirred for 24 hours. The solvent is removed in vacuo, and the residue is triturated with isopropyl ether and is filtered off with suction. 30.8 g (60%) of the title compound are obtained as colorless crystals of melting point 171° C.

$^1$H-NMR(CDCl$_3$): δ=7.3–6.6 (m,8H); 4.92 (s,1H); 3.72 (s,3H) ppm.

Calculated ($C_{15}H_{13}NO_2S$): C, 66.4; H,4.8; N,5.2. Found C, 66.6; H, 4.8; N, 5.0.

(d) 2,3-Dihydro-2,4-dimethyl-2-(2-methoxyphenyl)benzothiazin-3-one 4.8 g of sodium hydride (50% in oil) are washed 3 x with hexane to remove the oil, and are then dried in a stream of $N_2$. After suspending it in 40 ml of dry dimethylformamide, 10 g (36.9 mmol) of 2,3-dihydro-2-(2-methoxyphenyl)benzothiazin-3-one in 10 ml of dry DMF are added dropwise. After stirring for 30 min, 6.8 ml of methyl iodide are added, with cooling, and the mixture is stirred for 2.5 hours. It is then poured on ice and extracted with $CH_2Cl_2$. The organic phase is dried with $Na_2SO_4$ and concentrated. The crude product is chromatographed on silica gel using ethyl acetate/cyclohexane (1:3). 10.1 g of the title compound are obtained as colorless crystals of melting point 78° C.

$^1$H-NMR(CDCl$_3$): δ=7.5–6.5 (m,8H); 3.77 (s,3H); 3.15 (s,3H); 1.83 (s,3H) ppm.

Calculated ($C_{17}H_{17}NO_2S$): C, 68.2; H,5.7; N,4.6. Found: C, 68.5; H, 5.7; N, 4.6.

(e) 2,3-Dihydro-2,4-dimethyl-2-(2-hydroxyphenyl)benzothiazin-3-one 5.2 ml of boron tribromide solution (1M in hexane) are added to 1.85 g (6.2 mmol) of 2,3-dihydro-2,4-dimethyl-2-(2-methoxyphenyl)benzothiazin-3-one in 20 ml of absolute methylene chloride at 0 degrees centigrade. After 2 hours at room temperature, the mixture is poured onto water, and the precipitated colorless solid is extracted with ethyl acetate. After drying with $MgSO_4$, the solution is concentrated and the residue is triturated with isopropyl ether. 1.45 g of colorless crystals of melting point 164° to 167° C. are obtained.

$^1$H-NMR(CDCl$_3$): δ=7.5–6.5 (m,9H); 3.53 (s,3H); 1.90 (s,3H) ppm.

Calculated ($C_{16}H_{15}NO_2S$): C, 67.3; H,5.3; N,4.9. Found: C, 66.5; H, 5.4; N, 4.9.

(f) 2,3-Dihydro-2,4-dimethyl-2-[2-(4-chlorobutoxy)-phenyl]-benzothiazin-3-one 1.4 g (5 mmol) of the compound from (e) are dissolved together with 0.58 ml (5 mmol) of 1-bromo-4-chlorobutane and 0.97 g (7 mmol) of potassium carbonate in 30 ml of methyl ethyl ketone, and the solution is heated to reflux for 8 hours. After filtration off and concentration, 2.04 g of the title compound are obtained as a yellow oil which can be used without further purification.

¹H-NMR(CDCl₃): δ=7.4-6.4 (m,8H); 3.9 (t,3H); 3.6 (t,3H); 3.4 (s,3H); 2.2-1.8 (m,4H); 1.85 (s,3H) ppm.

(g)
2,3-Dihydro-2,4-dimethyl-2-[2-[4-[N-[2-(3,4-dimethoxyphenyl)ethyl-N-methyl]amino]butoxy]phenyl]benzothiazin-3-one hydrochloride 2.04 g of the compound from (f) and 1.37 g of N-methylhomoveratrylamine together with 1.38 g of potassium carbonate in 30 ml of toluene are heated to reflux for 40 hours. After dilution with ethyl acetate, the organic phase is washed with saturated NaCl solution, dried with Na₂SO₄ and concentrated. The crude product is chromatographed on 230 g of silica gel using CH₂Cl₂/MeOH (15:1). After trituration with ethyl acetate/ether, 1.2 g of product of melting point 72°-75° C. is obtained.

¹H-NMR(CDCl₃): δ=7.6-6.5 (m,11H); 3.93 (t,3H); 3.83 (s,6H); 3.43 (s,3H); 3.5-3.0 (m, 6H); 2.87 (s,3H); 2.5-1.6 (m,4H); 1.75 (s,3H) ppm.

For conversion into the HCl salt, the product is taken up in acetone, and 2.5N ethanolic HCl is added. After concentration and trituration with ethyl acetate, 1.2 gram of crystals of melting point 147° to 150° C. is obtained.

Calculated (C₃₁H₃₉ClN₂O₄S.H₂O): C, 63.2; H, 7.0; N, 4.8. Found: C, 63.4; H, 6.8; N, 4.7.

EXAMPLE 2

2,3Dihydro-2,4-dimethyl-2-[2-[3-[N-[2-(3,4-dimethoxyphenyl)ethyl-N-methyl]amino]propoxy]phenyl]benzothiazin-3-one (a)
2,3-Dihydro-2,4-dimethyl-2-[2-(3-chloropropoxy)phenyl]benzothiazin-3-one 3.35 g of 2,3-dihydro-2,4-dimethyl-2-(2-hydroxyphenyl)benzothiazin-3-one are dissolved, together with 2.4 g (15.27 mmol) of 1-bromo-3-chloropropane and 3.25 g of potasssium carbonate, in 30 ml of methyl ethyl ketone, and the solution is heated to reflux for 15 hours. The precipitate is filtered off with suction, and the filtrate is concentrated. 4.8 g of crude product are obtained, and this crystallizes on standing, and is triturated with hexane and filtered off with suction; melting point 92° C.

(b)
2,3Dihydro-2,4-dimethyl-2-[2-[3-[N-[2-(3,4-dimethoxyphenyl)ethyl-N-methyl]amino]propoxyl]benzothiazin-3-one 1.45 g (4 mmol) of the compound from Example (2a), together with 1.37 g of N-methylhomoveratrylamine and 1.38 g of potassium carbonate, are added to 30 ml of toluene, and the mixture is heated to reflux for 40 hours. After dilution with ethyl acetate, the mixture is washed with water, extracted once more with ethyl acetate, and the organic phase is washed with saturated sodium chloride solution, dried over sodium sulfate and concentrated. After chromatography on silica gel using methylene chloride/methanol (13:1) as the mobile phase, 1.16 g (56%) of the title compound is obtained as an oil.

¹H-NMR(CDCl³): δ=7.5-6.5 (m,11H); 3.97 (t,3H); 3.83 (s,6H); 3.47 (s,3H); 2.75 (mc,6H); 2.4 (s,3H); 2.1-1.8 (m,2H); 1.83 (s,3H) ppm.

EXAMPLE 3

2,3-Dihydro-4-methyl-2-[2-[4-[N-[2-(3,4-dimethoxyphenyl)-ethyl-N-methyl]amino]butoxy]phenyl]benzothiazin-3-one hydrochloride (a)
2,3-Dihydro-4-methyl-2-(2-methoxyphenyl)benzothiazin-3-one 5.42 g (20 mmol) of 2,3-dihydro-2-(2-methoxyphenyl)benzothiazin-3-one are dissolved in 100 ml of acetone, and 6.9 ml of methyl iodide and 6.5 g of potassium carbonate are added, and the mixture is heated to reflux for 45 hours. After filtration, the filtrate is concentrated. The product crystallizes on trituration with isopropyl ether.

Melting point: 150°-152° C.
Yield: 5.95 g (100%).
¹H-NMR(CDCl₃): δ=7.4-6.6 (m,8H); 5.1 (s,1H); 3.83 (s,3H); 3.53 (s,3H) ppm.

(b)
2,3-Dihydro-4-methyl-2-(2-hydroxyphenyl)benzothiazin-3-one 5.8 g (20.4 mmol) of the compound from Example (3a) are dissolved in anhydrous methylene chloride and, at 0 degrees centigrade, 21.6 ml of boron tribromide solution (1M in hexane) are added dropwise. After 2 hours at room temperature, the mixture is poured onto 300 ml of ice-water, the organic phase is separated off, and the aqueous phase is extracted twice more with methylene chloride. The combined organic phases are washed with 3% strength NaHCO₃ solution and with saturated sodium chloride solution, dried with magnesium sulfate and concentrated. The crude crystals obtained on trituration with diethyl ether are recrystallized from toluene. 4.3 g of the title compound of melting point 162°-64° C. are obtained.

¹H-NMR(CDCl₃): δ=8.08 (s,1H); 7.6-6.6 (m,8H); 4.97 (s,1H); 3.49 (s,3H) ppm.

Calculated (C₁₅H₁₃NO₂S): C, 66.4; H, 4.8; N, 5.2. Found: C, 66.4; H, 4.6; N, 5.1.

(c)
2,3-Dihydro-4-methyl-2-[2-(4-bromobutoxy)phenyl]-benzothiazin-3-one 4.3 g (15.9 mmol) of the compound from Example (3b), together with 10.28 g (47.6 mmol) of 1,4-dibromobutane and 2.7 g (20 mmol) of potassium carbonate, in 80 ml of methyl ethyl ketone are heated to reflux for 15 hours. After filtering off the precipitate with suction, the filtrate is concentrated. The residue is chromatographed on silica gel using ethyl acetate/cyclohexane (1:3) as the mobile phase. 4.8 g (74%) of the title compound are obtained, and this crystallizes on trituration with ethyl acetate/isopropyl ether, melting point 93° C.

¹H-NMR(CDCl₃): δ=7.4-6.6 (m,8H); 5.05 (s,1H); 4.1-3.9 (m,2H); 3.50 (s,3H); 3.6-3.3 (m,2H); 2.4-1.8 (m,4H) ppm.

Calculated (C₁₉H₂₀BrNO₂S): C,56.2; H, 5.0; N, 3.5. Found: C, 56.1 H, 4.9; N, 3.4.

(d) 2,3-Dihydro-4-methyl-2-[2-[4-[N-[2-(3,4-dimethoxyphenyl)ethyl-N-methyl]amino butoxy]phenyl]benzothiazin-3-one oxalate 1.2 g (2.95 mmol) of the compound from Example (3c), together with 0.9 g (5 mmol) of N-methyl-homoveratrylamine and 0.83 g (6 mmol) of potassium carbonate, in 20 ml of isopropanol are heated to reflux for 15 hours. After filtering off the precipitate, the filtrate is concentrated and the crude product is chromatographed on silica gel using methylene chloride/cyclohexane (10:1). 1.4 g (91%) of the title compound is obtained as the free base.

$^1$H-NMR(CDCl$_3$): δ=7.4–6.6 (m,11H); 5.08 (s,1H); 4.02 (t,3H); 3.85+3.83 (2s,6H); 3.54 (s,3H); 3.0–2.4 (m,6H); 2.33 (s,3H) 2.0 –1.5 (m,4H) ppm.

To convert into the oxalate, the product is dissolved in acetone, and 10 ml of oxalic acid in ethanol are added, the mixture is concentrated and evaporated 2× with acetone, and then allowed to stand with ethyl acetate. 1.26 g of crystals of melting point 92°–93° C. are obtained.

EXAMPLE 4

2,3-Dihydro-4-phenyl-2-[2-[4-[N-[2-(3,4-dimethoxyphenyl)-ethyl-N-methyl]amino]butoxy]phenyl]benzothiazin-3-one hydrochloride 2,3-Dihydro-4-phenyl-2-(2-methoxyphenyl)benzothiazin-3-one 2.7 g of 2,3-dihydro-2-(2-methoxyphenyl)benzothiazin-3-one, together with 1.2 g of potassium acetate, 6 g of iodobenzene and copper on an aluminum oxide support as the catalyst, in 80 ml of mesitylene are heated at 160° C. for 6 hours under a water separator which is charged with 2 g of barium oxide and 5 g of silica gel. After filtration, the residue is washed with dilute ammonia, and the filtrate is concentrated and chromatographed on 100 g of silica gel using ispropyl ether. 2.6 g of crude product are obtained, and this crystallizes from isopropyl ether/a little acetone, melting point 133° C.

$^1$H-NMR(CDCl$_3$): δ=7.6–6.5 (m,13H); 5.27 (s,1H); 3.87 (s, 3H) ppm.

Calculated (C$_{21}$H$_{17}$NO$_2$S): C, 72.6; H,4.9; N,4.0. Found: C, 72.8; H, 5.0; N, 4.4.

(b) 2,3-Dihydro-4-phenyl-2-(2-hydroxyphenyl)benzothiazin-3-one 2.9 g (8.4 mmol) of the compound from Example 4a) are dissolved in 30 ml of dry methylene chloride and, at 0 degrees centigrade, 8.4 ml of boron tribromide solution (1M in hexane) are added dropwise. After 2 hours at room temperature, a further 8.4 ml of boron tribromide solution are added. After a further 30 min, the dark red solution is poured onto ice-water, and the mixture is stirred for 30 min and then extracted 3× with methylene chloride. After drying with MgSO$_4$, the solution is concentrated and the residue is triturated with isopropyl ether. The resulting yellow crystals are recrystallized from toluene. 1.85 g of the title compound are obtained as pale yellow crystals of melting point 165°–168° C.

$^1$H-NMR(CDCl$_3$): δ=7.6–6.3 (m,14H); 5.09 (s,1H) ppm.

Calculated (C$_{20}$H$_{15}$NO$_2$S): C,72.0; H, 4.5; N, 4.2. Found: C, 72.4; H, 4.6; N, 4.0.

(c) 2,3-Dihydro-4-phenyl-2-[2-(4-chlorobutoxy)phenyl]-benzothiazin-3-one 1.75 g (5.3 mmol) of the compound from Example (4c), together with 1.37 g (8 mmol) of 1-bromo-4-chlorobutane and 1.66 g of potassium carbonate, in 30 ml of methyl ethyl ketone are heated to reflux for 10 hours, then the precipitate is filtered off, and the filtrate is concentrated. The crude product is filtered through 30 g of silica gel using ethyl acetate, 2.3 g of the title compound being obtained as an oil.

$^1$H-NMR(CDCl$_3$): δ=7.6–6.5 (m,13H); 5.22 (s,1H); 4.2–3.9 (m,2H); 3.8–3.4 (m,2H); 2.4–1.6 (m,4H) ppm.

(d) 2,3- Dihydro-4-phenyl-2-[2-[4-[N-[2-(3,4-dimethoxyphenyl)ethyl-N-methyl]amino]butoxy]phenyl]benzothiazin-3-one hydrochloride 1.15 g (2.71 mmol) of the compound from Example 4d), together with 0.78 g (4 mmol) of N-methyl-homoveratrylamine and 0.83 g (6 mmol) of potassium carbonate, in 20 ml of isopropanol are heated to reflux for 40 hours. After filtering off the precipitate, the filtrate is concentrated and chromatographed on silica gel using methylene chloride/methanol (15:1). 0.75 g (47%) of the free base is obtained as a yellow oil. This is dissolved in acetone, and 2.5N HCl in ethanol (2 ml) is added. After concentration, the residue is triturated with acetone/ether. 0.5 g of colorless crystals of melting point 192°–195° C. is obtained.

$^1$H-NMR(CDCl$_3$): δ=7.6–6.5 (m,13H); 5.20 (s,1H); 4.15–3.9 (m,2H); 3.83 (s,6H); 2.9–2.5 (m,6H); 2.4 (s,3H); 2.0–1.6 (m,4H) ppm (free base).

(Calculated (C$_{35}$H$_{39}$ClN$_2$O$_4$S): C, 67.9; H, 6.4; N, 4.5. Found: C, 67.5; H, 6.4; N, 3.8.

EXAMPLE 5

2,3-Dihydro-2,4-dimethyl-2-[2-[4-[4-[2-(3,4,5-trimethoxyphenyl)ethyl]piperazinyl]butoxy]phenyl]benzothiazin-3-one bismaleate 1.5 g (4 mmol) of the compound from Example 1 (f), together with 1.12 g (4 mmol) of 3,4,5-trimethoxyphenylethylpiperazine, are heated at 120° C. for 4 hours. The resulting oil is taken up in ethyl acetate/1N NaOH, the mixture is extracted twice more with ethyl acetate, and the organic phase is dried with sodium sulfate, concentrated and the crude product is chromatographed on silica gel using methylene chloride/methanol (12:1) as the mobile phase. The resulting oil (0.6 g) crystallizes from ethyl acetate/ether on standing, melting point 176°–179° C.

$^1$H-NMR(CDCl$_3$): δ=7.6–6.5 (m,8H); 6.44 (s,2H); 4.1–3.9 (m,2H); 3.83 +3.80 (2s,9H); 3.47 (s,3H); 3.4–2.7 (m,14H); 2.5–1.7 (m,4H); 1.77 (s,3H) ppm.

The free base is taken up in methylene chloride, and 120 mg of maleic acid in 10 ml of acetone are added, the solution is concentrated, the residue is taken up in acetone, and the solid is filtered off with suction, melting point 158°–160° C.

EXAMPLE 6

2,3-Dihydro-2,4-dimethyl-2-[2-[3-[4-[2-(3,4,5-trimethoxyphenyl)ethyl]piperazinyl]propoxy]phenyl]benzothiazin-3-one bismaleate 1.45 g (4 mmol) of the compound from Example (2a), together with 1.12 g (4 mmol) of 3,4,5-trimethoxyphenylethylpiperazine, are heated at 120° C. for 4 hours. After working up in analogy to Example 5, 0.5 g of oil is obtained.

¹H-NMR(CDCl₃): =7.6–6.5 (m,8H); 6.43 (s,2H); 4.11–3.9 (m,2H); 3.83 +3.80 (2s,9H); 3.47 (s,3H); 3.2–2.5 (m,14H); 2.4–2.0 (m,2H); 1.80 (s,3H) ppm.

After taking up in CH₂Cl₂, 193 mg of maleic acid in 10 ml of acetone are added, the mixture is concentrated 2× with acetone, and the residue is taken up in acetone/diethyl ethyl ether, and finally the colorless crystals are filtered off with suction, melting point 157°–159° C.

EXAMPLE 7

2,3-Dihydro-4-phenyl-2-[2-[4-[4-[2-(3,4,5-trimethoxyphenyl)ethyl]piperazinyl]butoxy]phenyl]benzothiazin-3-one bismaleate 1.15 g of the compound from Example (4c), together with 0.84 g of 3,4,5-trimethoxyphenylethylpiperazine and 0.6 g of potassium carbonate, in 15 ml of isopropanol are heated to reflux for 48 hours. The precipitate is filtered off, washed with methylene chloride, and the filtrate is concentrated. Chromatography of the crude product on silica gel using methylene chloride/methanol (10:1) provides 0.8 g of colorless oil.

¹H-NMR(CDCl₃): δ=7.5–6.5 (m,13H); 6.43 (s,2H); 5.30 (s,1H); 4.05 (t,2H); 3.85+3.83 (2s,9H); 2.9–2.2 (m,14H); 2.0–1.6 (m,4H) ppm.

For conversion into the maleate, the product is taken up in CH₂Cl₂, 280 mg of maleic acid in 10 ml of acetone are added, and the mixture is concentrated and the residue is triturated with acetone. Colorless crystals of melting point 149°–150° C.

Calculated (C₄₇H₅₃N₃O₁₃S). C, 62,7; H, 5.9; N, 4.7. Found: C, 62.6; H, 5.9; N, 4.9.

EXAMPLE 8

2,3-Dihydro-2,4-dimethyl-2-[3-[4-[N-[3-(3,4-dimethoxyphenyl)-1-methylpropyl-N-methyl]amino]propoxy]phenyl]-benzothiazin-3-one 1.6 g of the compound from Example (2a), together with 0.99 g of N,1-dimethyl-3,4-dimethoxyphenylpropylamine and 0.6 ml of N-ethylmorpholine, in 20 ml of DMF are heated at 100° C. for 15 hours, and the mixture is diluted with water and methylene chloride and extracted 2× with methylene chloride. The combined organic phases are washed 5× with water, dried with sodium sulfate, and concentrated. Chromatography on silica gel using methylene chloride/methanol (10:1) provides 0.57 g of the title compound as a yellowish resin.

¹H-NMR(CDCl₃): δ=7.5–6.5 (m,11H); 3.99 (t,3H); 3.83 (s,oH); 3.43 (s,3H); 3.1–2.0 (m,5H); 2.4 (s,3H); 1.80 (s,3H); 10 +1.08 (2d,3H) ppm.

EXAMPLE 9

2,3-Dihydro-2,4-dimethyl-2-[2-[4-[N-[2-(3,4-dimethoxyphenyl)-ethyl-N-methyl]amino]butoxy]phenyl]benzothiazin-3-one hydrochloride 1.4 g (5 mmol) of the compound from Example (1e), together with 1.42 g (5 mmol) of 4-chloro-N-[2-(3,4-dimethoxyphenyl)ethyl-N-methyl]butylamine and 0.97 g (7 mmol) of potassium carbonate, in 20 ml of isopropanol are heated to reflux for 18 hours. After the customary work-up, the process is continued as in Example (1g). The analytical data of the resulting product agree with those of the compound from Example (1g).

EXAMPLE 10

2,3-Dihydro-2,4-dimethyl-2-[2-[4-[2-(3,4,5-trimethoxyphenyl)ethyl]piperazinyl]butoxy]phenyl]benzothiazin-3-one bismaleate 1.4 g (5 mmol) of the compound from Example 1e), together with 1.85 g (5 mmol) of N1-[2-(3,4,5-trimethoxyphenyl)ethy]-N2-4-chloro-1-butylpiperazine and 0.97 g (7 mmol) of um carbonate, are heated to reflux for 14 hours. After the usual work-up, and chromatography as described in Example 5, the title compound is obtained, and its physical data agree with those in Example 5.

By using suitable starting materials and reagents, the compounds listed in the tables below are obtained by applying the procedures described in Examples 1 to 10.

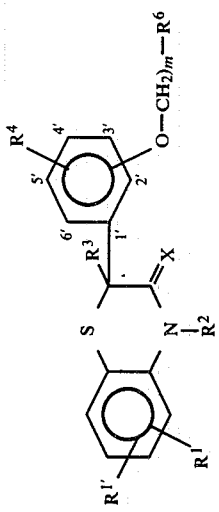
| Example No. | R¹ | R¹' | R² | R³ | R⁴ | R⁶ | m | X | Side chain in position | NMR (δ, ppm) |
|---|---|---|---|---|---|---|---|---|---|---|
| 11 | H | H | CH₃ | CH₃ | H | 4-OCH₃-C₆H₄-(CH₂)₂-N(CH₃)- | 3 | O | 2' | 7.5–6.5(m,12H);3.95(t,2H);3.87 (s,3H);3.47(s,3H);2.4(s,3H); 2.9–2.5(m,6H);2.1–1.8(m,2H); 1.86(s,3H). |
| 12 | H | H | CH₃ | CH₃ | H | 3-OCH₃-C₆H₄-(CH₂)₂-N(CH₃)- | 3 | O | 2' | 7.6–6.4(m,12H);3.92(t,2H);3.82 (s,3H);3.47(s,3H);2.9–2.5(m, 6H);2.42(s,3H);2.1–1.7(m,2H); 1.84(s,3H). |
| 13 | H | H | CH₃ | CH₃ | H | 3,4,5-(OCH₃)₃-C₆H₂-(CH₂)₂-N(CH₃)- | 3 | O | 2' | 7.4–6.6(m,10H);3.87+3.81(2s,9H); 4.05–3.8(m,2H);3.45(s,3H);2.9– 2.5(m,6H);2.46(s,3H);2.2–1.9 (m,2H);1.84(s,3H). |
| 14 | H | H | CH₃ | CH₃ | H | 3,5-(OCH₃)₂-C₆H₃-(CH₂)₂-N(CH₃)- | 3 | O | 2' | 7.5–6.6(m,11H);3.95(t,2H); 3.84(s,6H);3.47(s,3H);2.9–2.5 (m,6H);2.43(s,3H);2.1–1.8(m, 2H);1.83(s,3H). |

-continued

| Example No. | R¹ | R¹' | R² | R³ | R⁴ | R⁶ | m | X | Side chain in position | NMR (δ, ppm) |
|---|---|---|---|---|---|---|---|---|---|---|
| 15 | H | H | CH₃ | CH₃ | H | 2,3-dimethoxyphenyl with (CH₂)₂N(CH₃)₂ substituent | 3 | O | 2' | 7.4–6.5(m,10H);3.92(t,2H); 3.9–3.8(3s,3H);3.47(s,3H); 2.9–2.5(m,6H);2.41(s,3H);2.1– 1.8(m,2H);1.86(s,3H). |
| 16 | H | H | CH₃ | CH₃ | H | 2-methoxyphenyl with (CH₂)₂N(CH₃)₂ substituent | 3 | O | 2' | 7.6–6.5(m,12H);3.93(t,2H);3.84 (s,3H);3.47(s,3H);2.95–2.5(m, 6H);2.42(s,3H);2.1–1.8(m,2H); 1.85(s,3H). |
| 17 | H | H | CH₃ | CH₃ | H | 2,4-dimethoxyphenyl with (CH₂)₂N(CH₃)₂ substituent | 3 | O | 2' | 7.5–6.6(m,11H);3.95(t,2H); 3.84(s,6H);3.44(s,3H); 2.9–2.5(m,6H);2.47(s,3H); 2.1–1.8(m,2H);1.82(s,3H). |
| 18 | H | H | CH₃ | CH₃ | H | 3,4,5-trimethoxyphenyl with CH(CH₃)N(CH₃)₂ substituent | 3 | O | 2' | 7.5–6.4(m,10H);3.93(t,2H); 3.87(s,9H);3.47(s,3H);2.9– 2.5(m,5H);2.47(s,3H);2.1– 1.8(m,2H);1.84(s,3H);1.15 (d,3H). |

-continued

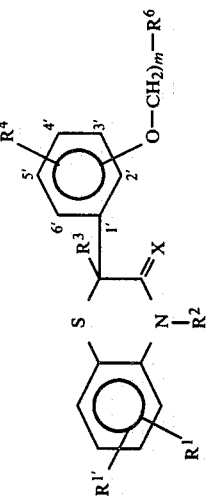

| Example No. | $R^1$ | $R^{1'}$ | $R^2$ | $R^3$ | $R^4$ | $R^6$ | m | X | Side chain in position | NMR (δ, ppm) |
|---|---|---|---|---|---|---|---|---|---|---|
| 19 | H | H | CH$_3$ | CH$_3$ | H | —N-CH-CH$_2$-(3,4-(OCH$_3$)$_2$-C$_6$H$_3$), CH$_3$ | 3 | O | 2' | 7.5-6.5(m,11H);3.93(t,2H); 3.84(s,6H);3.47(s,3H);2.9- 2.5(m,5H);2.43(s,3H);2.1- 1.8(m,2H);1.87(s,3H);1.14 (d,3H). |
| 20 | H | H | CH$_3$ | CH$_3$ | H | —N-CH-CH$_2$-(4-OCH$_3$-C$_6$H$_4$), CH$_3$ | 3 | O | 2' | 7.6-6.5(m,12H);3.97(t,2H); 3.87(s,3H);3.44(s,3H);2.9- 2.5(m,5H);2.47(s,3H);2.1- 1.8(m,2H);1.81(s,3H);1.19 (d,3H). |
| 21 | H | H | CH$_3$ | CH$_3$ | H | —N-CH-CH$_2$-(3-OCH$_3$-C$_6$H$_4$), CH$_3$ | 3 | O | 2' | 7.6-6.5(m,12H);3.94(t,2H); 3.84(s,3H);3.47(s,3H);2.9- 2.5(m,5H);2.41(s,3H);2.1- 1.8(m,2H);1.84(s,3H);1.21 (d,3H). |
| 22 | H | H | CH$_3$ | CH$_3$ | H | —N-(CH$_2$)$_2$-(3,4-(OCH$_3$)$_2$-C$_6$H$_3$), H | 3 | O | 2' | 7.5-5.5(m,11H);3.92(t,2H); 3.87(s,6H);3.47(s,3H);2.9- 2.5(m,6H);2.1-1.8(m,2H); 1.83(s,3H). |
| 23 | H | H | CH$_3$ | CH$_3$ | H | —N-(CH$_2$)$_2$-(3,4,5-(OCH$_3$)$_3$-C$_6$H$_2$), H | 3 | O | 2' | 7.4-6.4(m,10H);3.9(t,2H);3.83 (s,9H);3.47(s,3H);2.9-2.5(m,6H); 2.1-1.8(m,2H);1.84(s,3H). |

-continued
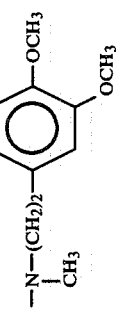
| Example No. | R¹ | R¹' | R² | R³ | R⁴ | R⁶ | m | X | Side chain in position | NMR (δ, ppm) |
|---|---|---|---|---|---|---|---|---|---|---|
| 24 | H | H | CH₃ | CH₃ | H | 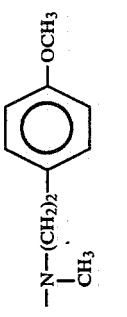 | 4 | O | 2' | 7.4–6.4(m,10H);3.9(t,2H);3.87+3.81(2s,9H);3.45(s,3H);2.9–2.5 (m,6H);2.47(s,3H);2.3–1.8(m, 4H);1.84(s,3H). |
| 25 | H | H | CH₃ | CH₃ | H | 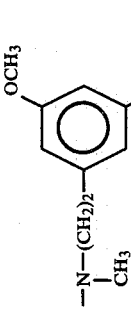 | 4 | O | 2' | 7.5–6.5(m,12H);3.95(t,2H);3.87. (s,3H);3.47(s,3H);2.9–2.5(m, 6H);2.4(s,3H);2.3–1.8(m,4H); 1.86(s,3H). |
| 26 | H | H | CH₃ | CH₃ | H | 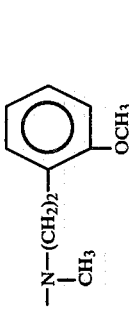 | 4 | O | 2' | 7.5–6.6(m,11H);3.95(t,2H);3.84 (s,6H);3.47(s,3H);2.9–2.5(m,6H); 2.43(s,3H);2.3–1.7(m,4H);1.83 (s,3H). |
| 27 | H | H | CH₃ | CH₃ | H |  | 4 | O | 2' | 7.5–6.5(m,12H);3.82 (s,3H);3.95(t,2H);2.9–2.5(m, 6H);2.41(s,3H);2.3–1.7(m,4H); 1.84(s,3H). |

-continued
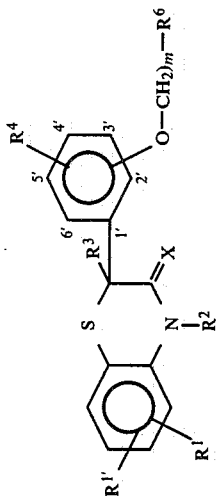
| Example No. | $R^1$ | $R^{1'}$ | $R^2$ | $R^3$ | $R^4$ | $R^6$ | m | X | Side chain in position | NMR (δ, ppm) |
|---|---|---|---|---|---|---|---|---|---|---|
| 28 | H | H | CH$_3$ | CH$_3$ | H | —N—(CH$_2$)$_2$—[2,4-di-OCH$_3$-phenyl], N-CH$_3$ | 4 | O | 2' | 7.5–6.5(m,11H);3.94(t,2H);3.82(s,6H);3.46(s,3H);2.40(s,3H);2.9–2.5(m,6H);2.3–1.7(m,4H);1.86(s,3H). |
| 29 | H | H | CH$_3$ | CH$_3$ | H | —N—CH—CH$_2$—[3,4,5-tri-OCH$_3$-phenyl], CH$_3$ | 4 | O | 2' | 7.5–6.44(m,10H);3.93(t,2H);3.89+3.83(2s,9H);3.47(s,3H);2.9–2.5(m,5H);2.46(s,3H);2.1–1.7(m,4H);1.84(s,3H);1.05(d,3H). |
| 30 | H | H | CH$_3$ | CH$_3$ | H | —N—CH—CH$_2$—[3,4-di-OCH$_3$-phenyl], CH$_3$ | 4 | O | 2' | 7.5–6.5(m,11H);3.93(t,2H);3.84(s,6H);3.47(s,3H);2.9–2.5(m,5H);2.44(s,3H);2.3–1.7(m,4H);1.86(s,3H);1.07(d,3H). |
| 31 | H | H | CH$_3$ | CH$_3$ | H | —N—CH—CH$_2$—[4-OCH$_3$-phenyl], CH$_3$ | 4 | O | 2' | 7.5–6.5(m,12H);3.90(t,2H);3.86(s,3H);3.46(s,3H);2.9–2.5(m,5H);2.44(s,3H);2.3–1.7(m,4H);1.84(s,3H);1.04(d,3H). |

-continued
| Example No. | R¹ | R¹' | R² | R³ | R⁴ | R⁶ | m | X | Side chain in position | NMR (δ, ppm) |
|---|---|---|---|---|---|---|---|---|---|---|
| 32 | H | H | CH₃ | CH₃ | H | 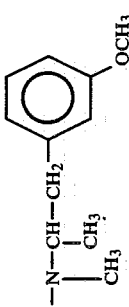 | 4 | O | 2' | 7.5–6.4(m,12H);3.94(t,2H);3.81 (s,3H);3.47(s,3H);2.9–2.5(m,5H); 2.46(s,3H);2.3–1.7(m,4H);1.86 (s,3H);1.08(d,3H). |
| 33 | H | H | CH₃ | CH₃ | H |  | 4 | O | 2' | 7.5–6.5(m,11H);3.94(t,2H);3.84 (s,6H);3.47(s,3H);2.9–2.5(m,5H); 2.40(s,3H);2.3–1.7(m,4H);1.84(s, 3H);1.06(d,3H). |
| 34 | H | H | CH₃ | CH₃ | H |  | 4 | O | 2' | 7.5–6.5(m,11H);3.92(t,2H);3.87 (s,6H);3.47(s,3H);2.9–2.5(m,6H); 2.5–1.8(m,4H);1.83(s,3H). |
| 35 | H | H | CH₃ | CH₃ | H | 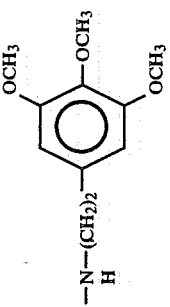 | 4 | O | 2' | 7.5–6.4(m,10H);3.94(t,2H);3.88 + 3.82(2s,9H);3.47(s,3H);2.9–2.5 (m,6H);2.5–1.8(m,4H);1.83(s,3H). |

-continued

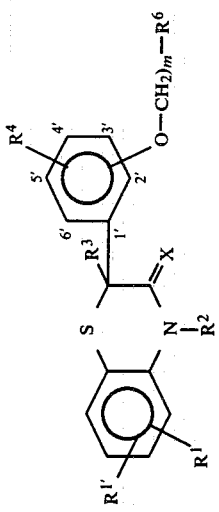

| Example No. | $R^1$ | $R^{1'}$ | $R^2$ | $R^3$ | $R^4$ | $R^6$ | m | X | Side chain in position | NMR (δ, ppm) |
|---|---|---|---|---|---|---|---|---|---|---|
| 36 | H | H | CH$_3$ | CH$_3$ | H | -N(H)-(CH$_2$)$_2$- (4-OCH$_3$-C$_6$H$_4$) | 4 | O | 2' | 7.5-6.5(m,12H);3.92(t,2H);3.84 (s,3H);3.44(s,3H);3.2-2.8(m,6H); 2.5-1.8(m,4H);1.83(s,3H). |
| 37 | H | H | CH$_3$ | CH$_3$ | H | -N(H)-(CH$_2$)$_2$- (3-OCH$_3$-C$_6$H$_4$) | 4 | O | 2' | 7.5-6.4(m,12H);3.94(t,2H);3.86 (s,3H);3.48(s,3H);3.2-2.7(m,6H); 2.4-1.7(m,4H);1.79(s,3H). |
| 38 | H | H | CH$_3$ | CH$_3$ | H | -N(H)-(CH$_2$)$_2$-(3,4-methylenedioxyphenyl) | 4 | O | 2' | 7.5-6.4(m,11H);5.05(s,2H);3.90 (t,2H);3.48(s,3H);3.1-2.7(m,6H); 2.4-1.8(m,4H);1.80(s,3H). |
| 39 | H | H | CH$_3$ | CH$_3$ | H | -N(H)-CH(CH$_3$)-CH$_2$-(3,4-di-OCH$_3$-C$_6$H$_3$) | 4 | O | 2' | 7.5-6.5(m,11H);3.96(t,2H);3.84 (s,6H);3.52(s,3H);3.4-3.0(m,6H); 2.4-1.8(m,4H);1.84(s,3H);1.12 (d,3H). |
| 40 | H | H | CH$_3$ | CH$_3$ | H | -N(H)-CH(CH$_3$)-CH$_2$-(3,4,5-tri-OCH$_3$-C$_6$H$_2$) | 4 | O | 2' | 7.5-6.3(m,10H);3.92(t,2H);3.83+ 3.80(2s,9H);3.50(s,3H);3.4-2.9 (m,6H);2.4-1.8(m,4H);1.82(s,3H); 1.05(d,3H). |

-continued
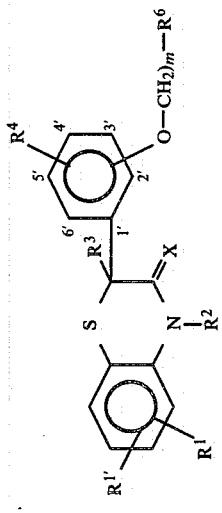
| Example No. | R¹ | R¹' | R² | R³ | R⁴ | R⁶ | m | X | Side chain in position | NMR (δ, ppm) |
|---|---|---|---|---|---|---|---|---|---|---|
| 41 | H | H | CH₃ | CH₃ | H | -N-CH-CH₂-<br>H  CH₃ / (4-OCH₃-C₆H₄) | 4 | O | 2' | 7.5–6.6(m,12H);3.94(t,2H);3.84(s,3H);3.51(s,3H);3.4–2.8(m,6H);2.4–1.8(m,4H);1.82(s,3H);1.08(d,3H). |
| 42 | H | H | CH₃ | CH₃ | H | -N-CH-CH₂-<br>H  CH₃ / (3-OCH₃-C₆H₄) | 4 | O | 2' | 7.5–6.6(m,12H);3.91(t,2H);3.84(s,3H);3.47(s,3H);4.3–2.7(m,6H);2.4–1.8(m,4H);1.84(s,3H);1.04(d,3H). |
| 43 | H | H | CH₃ | CH₃ | H | -N-CH-CH₂-<br>H  CH₃ / (3,5-(OCH₃)₂-C₆H₃) | 4 | O | 2' | 7.5–6.5(m,11H);3.94(t,2H);3.82(s,6H);3.46(s,3H);3.4–2.9(m,6H);2.3–1.7(m,4H);1.79(s,3H);1.14(d,JH). |
| 44 | H | H | CH₃ | CH₃ | H | -CH₂-(3-pyridyl) | 4 | O | 2' | 8.4–6.5(m,12H);4.3(s,2H);3.91(t,2H);3.4–2.9(m,4H);2.3–1.7(m,4H);1.79(s,3H). |
| 45 | H | H | CH₃ | CH₃ | H | -N(piperazinyl)-(CH₂)₂-(3,4-(OCH₃)₂-C₆H₃) | 3 | O | 2' | 7.6–6.5(m,11H);4.1–3.9(m,2H);3.84(s,6H);3.47(s,3H);3.2–2.5(m,14H);2.4–2.0(m,2H);1.81(s,3H). |

-continued

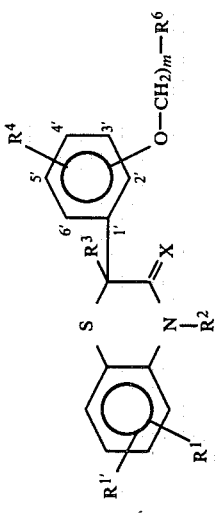

| Example No. | R¹ | R¹' | R² | R³ | R⁴ | R⁶ | m | X | Side chain in position | NMR (δ, ppm) |
|---|---|---|---|---|---|---|---|---|---|---|
| 46 | H | H | CH₃ | CH₃ | H | -N(piperazine)N-(CH₂)₂-C₆H₄-OCH₃ (4-OCH₃) | 3 | O | 2' | 7.6-6.5(m,12H);4.1-3.9(m,2H);3.86(s,3H);3.42(s,3H);3.2-2.5(m,14H);2.4-2.0(m,2H);1.79(s,3H). |
| 47 | H | H | CH₃ | CH₃ | H | -N(piperazine)N-(CH₂)₂-C₆H₃(OCH₃)₂ (3,4-diOCH₃) | 4 | O | 2' | 7.4-6.5(m,11H);4.1-3.8(m,2H);3.83(s,6H);3.47(s,3H);3.4-2.6(m,14H);2.5-1.7(m,4H);1.78(s,3H). |
| 48 | H | H | CH₃ | CH₃ | H | -N(piperazine)N-(CH₂)₂-C₆H₄-OCH₃ (4-OCH₃) | 4 | O | 2' | 7.6-6.5(m,12H);4.1-3.9(m,2H);3.81(s,3H);3.46(s,3H);3.1-2.1(m,14H);2.0-1.5(m,4H);1.80(s,3H). |
| 49 | H | H | CH₃ | CH₃ | H | -N(piperazine)N-(CH₂)₂-C₆H₃(OCH₃)₂ (2,4-diOCH₃) | 4 | O | 2' | 7.6-6.4(m,10H);4.1-3.9(m,2H);3.80(s,9H);3.47(s,3H);3.4-2.6(m,14H);2.4-1.7(m,4H);1.76(s,3H). |
| 50 | H | H | CH₃ | CH₃ | H | -N(piperazine)N-(CH₂)₂-C₆H₃(OCH₃)₂ (3,4-diOCH₃) | 4 | O | 2' | 7.5-6.4(m,10H);4.1-3.9(m,2H);3.82(s,9H);3.45(s,3H);3.3-2.6(m,14H);2.4-1.7(m,4H);1.80(s,3H). |

-continued
| Example No. | R¹ | R¹' | R² | R³ | R⁴ | R⁶ | m | X | Side chain in position | NMR (δ, ppm) |
|---|---|---|---|---|---|---|---|---|---|---|
| 51 | H | H | CH₃ | CH₃ | H | ![piperazine-trimethoxyphenyl] | 4 | O | 2' | 7.5–6.2(m,10H);4.1–3.9(m,2H);3.86 3.81(2s,9H);3.47(s,3H);3.4–2.5 (m,10H);2.4–1.7(m,4H);1.78(s,3H). |
| 52 | H | H | CH₃ | CH₃ | H | ![4-hydroxy-4-(dimethoxyphenethyl)piperidine] | 4 | O | 2' | 7.5–6.5(m,11H);4.1–3.9(m,2H); 3.83(s,6H);3.47(s,3H);3.4–2.9 (m,8H);2.4–1.5(m,10H);1.80(s,3H). |
| 53 | H | H | CH₃ | CH₃ | H | ![4-hydroxy-4-(dimethoxyphenyl)piperidine] | 4 | O | 2' | 7.5–6.5(m,11H);4.1–3.9(m,2H);3.84 (s,6H);3.45(s,3H);3.4–2.7(m,6H); 2.4–1.5(m,4H);1.77(s,3H). |
| 54 | H | H | CH₃ | CH₃ | H | ![tetrahydropyridine-trimethoxyphenethyl] | 4 | O | 2' | 7.5–6.4(m,10H);5.7(m,1H);4.1–3.9 (m,2H);3.85+3.80(2s,9H);3.45(s, 3H);3.4–2.6(m,12H);2.4–1.5(m,4H); 1.79(s,3H). |
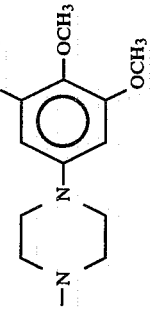

-continued

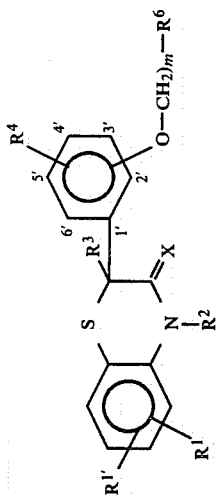

| Example No. | $R^1$ | $R^{1'}$ | $R^2$ | $R^3$ | $R^4$ | $R^6$ | m | X | Side chain in position | NMR (δ, ppm) |
|---|---|---|---|---|---|---|---|---|---|---|
| 55 | H | H | CH₃ | CH₃ | H | 3,4,5-tri-OCH₃-phenyl-(CH₂)₂-N-piperidinyl | 4 | O | 2' | 7.5–6.4(m,10H);4.1–3.9(m,2H); 3.86+3.80(2s,9H);3.47(s,3H); 3.4–2.6(m,8H);2.4–1.5(m,11H); 1.81(s,3H). |
| 56 | H | H | CH₃ | CH₃ | H | 3,4,5-tri-OCH₃-phenyl-(CH₂)₂-N(CH₃)– | 4 | O | 2' | 7.6–6.5(m,10H);4.1–3.9(m,2H); 3.84(s,6H);3.47(s,3H);2.9–2.5 (m,6H);2.4(s,3H);2.3(s,3H); 2.4–1.8(m,4H);1.84(s,3H). |
| 57 | H | H | CH₃ | CH₃ | H | 3,4-di-OCH₃-phenyl-(CH₂)₂-N(CH₃)– | 4 | O | 2' | 7.6–6.5(m,11H);4.1–3.9(m,2H); 3.82(s,3H);3.46(s,3H);2.9–2.5 (m,6H);2.4(s,3H);2.4–1.8(m,4H); 1.79(s,3H). |
| 58 | H | H | CH₃ | CH₃ | H | 3-Cl-4-OCH₃-phenyl-(CH₂)₂-N(CH₃)– | 4 | O | 2' | 7.6–6.6(m,11H);4.1–3.9(m,2H); 3.86(s,3H);3.51(s,3H);3.2–2.5 (m,6H);2.4(s,3H);2.3–1.7(m,4H); 1.81(s,3H). |
| 59 | H | H | CH₃ | CH₃ | H | 2-pyridyl-N-piperazinyl | 4 | O | 2' | 8.4–6.9(m,12H);4.1–3.9(m,2H); 3.50(s,3H);3.5–2.5(m,10H);2.3–1.6 (m,4H);1.80(s,3H). |

-continued

| Example No. | R¹ | R¹' | R² | R³ | R⁴ | R⁶ | m | X | Side chain in position | NMR (δ, ppm) |
|---|---|---|---|---|---|---|---|---|---|---|
| 60 | H | H | CH₃ | CH₃ | H | piperazinyl with N-pyrimidin-2-yl | 4 | O | 2' | 8.3–7.1(m,11H);4.1–3.9(m,2H); 3.46(s,3H);3.5–2.5(m,10H);2.3–1.6 (m,4H);1.78(s,3H). |
| 61 | H | H | CH₃ | CH₃ | H | piperazinyl-N-CO-(3,4-dimethoxyphenyl) | 4 | O | 2' | 7.6–6.8(m,11H);4.1–3.7(m,6H); 3.51(s,3H);3.5–2.5(m,6H);2.3–1.6 (m,4H);1.82(s,3H). |
| 62 | H | H | CH₃ | CH₃ | H | piperazinyl-N-CO-(3,4,5-trimethoxyphenyl) | 4 | O | 2' | 7.5–6.6(m,10H);4.1–3.7(m,6H); 3.51(s,3H);3.4–2.5(m,6H);2.3–1.6 (m,4H);1.84(s,3H). |
| 63 | 6-Cl | H | CH₃ | CH₃ | H | -N(CH₃)-(CH₂)₂-(3,4,5-trimethoxyphenyl) | 4 | O | 2' | 7.7–6.4(m,9H);4.1–3.9(m,2H);3.47 (s,3H);3.84+3.80(2s,9H);3.4–2.6(m, 6H);2.41(s,3H);2.3–1.7(m,4H);1.84 (s,3H). |

-continued

[Structure: general formula with R¹, R¹', R², R³, R⁴ substituents on benzothiazine-like core with side chain O—(CH₂)ₘ—R⁶ at positions 2'-6']

| Example No. | R¹ | R¹' | R² | R³ | R⁴ | R⁶ | m | X | Side chain in position | NMR (δ, ppm) |
|---|---|---|---|---|---|---|---|---|---|---|
| 64 | 6-Cl | H | CH₃ | CH₃ | H | —N(CH₂)₂—(3,4-dimethoxyphenyl), N-CH₃ | 4 | O | 2' | 7.6–6.5(m,10H);4.1–3.9(m,2H); 3.83(s,6H);3.47(s,3H);3.4–2.6 (m,6H);2.42(s,3H);2.3–1.7(m,4H); 1.79(s,3H). |
| 65 | 6-Cl | H | CH₃ | CH₃ | H | piperidinyl-(CH₂)₂—(3,4,5-trimethoxyphenyl) | 4 | O | 2' | 7.4–6.4(m,9H);4.1–3.9(m,2H);3.86+ 3.81(2s,9H);3.46(s,3H);3.4–2.5 (m,14H);2.4–1.7(m,4H);1.79(s, 3H). |
| 66 | H | 7-Cl | CH₃ | CH₃ | H | piperidinyl-(CH₂)₂—(3,4-dimethoxyphenyl) | 4 | O | 2' | 7.4–6.4(m,10H);4.1–3.9(m,2H); 3.87(s,6H);3.47(s,3H);3.4–2.5 (m,14H);2.4–1.7(m,4H);1.82(s,3H). |
| 67 | H | 7-F | CH₃ | CH₃ | H | —N(CH₂)₂—(3,4-dimethoxyphenyl), N-CH₃ | 4 | O | 2' | 7.4–6.5(m,10H);4.1–3.9(m,2H);3.86 (s,6H);3.47(s,3H);3.4–2.6(m,6H); 2.44(s,3H);2.3–1.7(m,4H);1.81(s, 3H). |

-continued
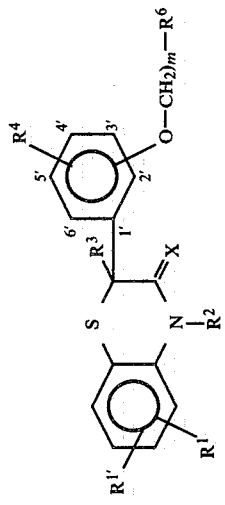
| Example No. | $R^1$ | $R^{1'}$ | $R^2$ | $R^3$ | $R^4$ | $R^6$ | m | X | Side chain in position | NMR (δ, ppm) |
|---|---|---|---|---|---|---|---|---|---|---|
| 68 | H | 7-F | CH₃ | CH₃ | H | (3,4,5-trimethoxyphenyl)-piperidinyl-N-(CH₂)₂- | 4 | O | 2' | 7.4–6.4(m,9H);4.1–3.9(m,2H);3.86+3.81(2s,9H);3.45(s,3H);3.3–2.5(m,14H);2.4–1.8(m,4H);1.86(s,3H). |
| 69 | 6-F | H | CH₃ | CH₃ | H | (3,4,5-trimethoxyphenyl)-N(CH₃)-(CH₂)₂- | 4 | O | 2' | 7.4–6.4(m,9H);4.1–3.9(m,2H);3.87+3.81(2s,9H);3.47(s,3H);3.3–2.4(m,6H);2.43(s,3H);2.3–1.7(m,4H);1.83(s,3H). |
| 70 | 6-F | H | CH₃ | CH₃ | H | (3,4-dimethoxyphenyl)-piperidinyl-N-(CH₂)₂- | 4 | O | 2' | 7.4–6.4(m,10H);4.1–3.9(m,2H);3.82(s,6H);3.44(s,3H);3.4–2.5(m,14H);2.3–1.7(m,4H);1.79(s,3H). |
| 71 | 6-OCH₃ | H | CH₃ | CH₃ | H | (4-methoxyphenyl)-N(CH₃)-(CH₂)₂- with OCH₃ | 4 | O | 2' | 7.4–6.4(m,10H);4.1–3.9(m,2H);3.84+3.81(2s,9H);3.39(s,3H);3.4–2.5(m,6H);2.44(s,3H);2.3–1.7(m,4H);1.82(s,3H). |

-continued

General structure:

R¹'—[benzene ring with R¹]—S—C(R³)—C(=X)—N(R²)—[benzene with R⁴ at 4', and O-(CH₂)ₘ-R⁶ at 2']

| Example No. | R¹ | R¹' | R² | R³ | R⁴ | R⁶ | m | X | Side chain in position | NMR (δ, ppm) |
|---|---|---|---|---|---|---|---|---|---|---|
| 72 | 6-OCH₃ | H | CH₃ | CH₃ | H | 3,4,5-tri-OCH₃-C₆H₂-N(piperazine)-(CH₂)₂- | 4 | O | 2' | 7.4–6.4(m,9H);4.1–3.9(m,2H); 3.9–3.8(3s,12H);3.44(s,3H);3.4–2.5(m,14H);2.3–1.7(m,4H);1.84(s,3H). |
| 73 | 6-CH₃ | H | CH₃ | CH₃ | H | 3,4-di-OCH₃-C₆H₃-N(CH₃)-(CH₂)₂- | 4 | O | 2' | 7.5–6.5(m,10H);4.1–3.9(m,2H);3.82(s,6H);3.51(s,3H);3.4–2.5(m,6H);2.44(s,3H);2.28(s,3H);2.3–1.7(m,4H);1.81(s,3H). |
| 74 | 6-CH₃ | H | CH₃ | CH₃ | H | 3,4-di-OCH₃-C₆H₃-N(piperazine)-(CH₂)₂- | 4 | O | 2' | 7.5–6.5(m,10H);4.1–3.9(m,2H);3.84(s,6H);3.50(s,3H);3.4–2.5(m,14H);2.29(s,3H);2.3–1.7(m,4H);1.81(s,3H). |
| 75 | 6-CH₃ | 7-CH₃ | CH₃ | CH₃ | H | 3,4-di-OCH₃-C₆H₃-N(piperazine)-(CH₂)₂- | 4 | O | 2' | 7.4–6.4(m,8H);4.1–3.9(m,2H);3.87+3.82(2s,9H);3.48(s,3H);3.4–2.6(m,14H);2.31(s,6H);2.3–1.7(m,4H);1.79(s,3H). |

-continued
| Example No. | $R^1$ | $R^{1'}$ | $R^2$ | $R^3$ | $R^4$ | $R^6$ | m | X | Side chain in position | NMR (δ, ppm) |
|---|---|---|---|---|---|---|---|---|---|---|
| 76 | H | 7-CH₃ | CH₃ | CH₃ | H | 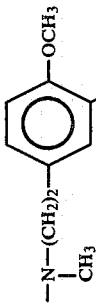 | 4 | O | 2' | 7.4–6.5(m,10H);4.1–3.9(m,2H);3.81 (s,6H);3.51(s,3H);3.4–2.6(m,6H); 2.45(s,3H);2.28(s,3H);2.3–1.7 (m,4H);1.78(s,3H). |
| 77 | H | H | C₂H₅ | C₂H₅ | H | 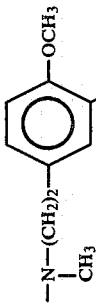 | 4 | O | 2' | 7.5–6.5(m,11H);4.1–3.7(m,4H);3.83 (s,6H);3.4–2.5(m,6H);2.46(s,3H); 2.3–1.7(m,6H);1.3(2t,6H). |
| 78 | H | H | C₂H₅ | CH₃ | H |  | 4 | O | 2' | 7.5–6.4(m,10H);4.1–3.7(m,4H);3.87 + 3.81(2s,9H);3.4–2.5(m,14H);2.46 (s,3H);2.3–1.7(m,4H);1.81(s,3H); 1.3(t,3H). |
| 79 | H | H | CH₃ | C₂H₅ | H |  | 4 | O | 2' | 7.5–6.5(m,12H);4.1–3.9(m,2H);3.81 (s,3H);3.51(s,3H);3.4–2.5(m,6H); 2.41(s,3H);2.3–1.7(m,6H);1.3 (t,3H). |

-continued
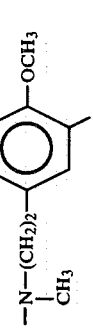
| Example No. | R¹ | R¹' | R² | R³ | R⁴ | R⁶ | m | X | Side chain in position | NMR (δ, ppm) |
|---|---|---|---|---|---|---|---|---|---|---|
| 80 | H | H | CH₃ | H | H | -N(CH₃)-(CH₂)₂- (3,4,5-trimethoxyphenyl) | 4 | O | 2' | 7.5-6.5(m,10H);5.10(s,1H);3.86+3.80(2s,9H);4.1-3.9(m,2H);3.47(s,3H);3.4-2.5(m,6H);2.4(s,3H);2.3-1.7(m,4H). |
| 81 | H | H | CH₃ | H | H | piperazinyl-(CH₂)₂-(3,4,5-trimethoxyphenyl) | 4 | O | 2' | 7.4-6.4(m,10H);5.10(s,1H);3.86+3.80(2s,9H);4.1-3.9(m,2H);3.46(s,3H);3.4-2.5(m,14H);2.3-1.7(m,4H). |
| 82 | H | H | CH₃ | H | H | piperazinyl-(CH₂)₂-(3,4-dimethoxyphenyl) | 4 | O | 2' | 7.4-6.5(m,11H);5.08(s,1H);3.81(s,6H);4.1-3.9(m,2H);3.51(s,3H);3.4-2.5(m,14H);2.3-1.7(m,4H). |
| 83 | H | H | CH₃ | H | H | -N(CH₃)-CH(CH₃)-CH₂-(3,4,5-trimethoxyphenyl) | 4 | O | 2' | 7.4-6.4(m,10H);4.1-3.9(m,2H);5.06(s,1H);3.87+3.82(2s,9H);3.49(s,3H);3.4-2.5(m,5H);2.48(s,3H);2.4-1.8(m,4H);1.06(d,3H). |

-continued
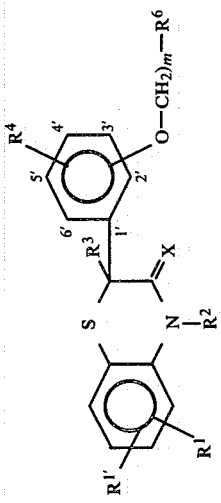
| Example No. | R¹ | R¹' | R² | R³ | R⁴ | R⁶ | m | X | Side chain in position | NMR (δ, ppm) |
|---|---|---|---|---|---|---|---|---|---|---|
| 84 | H | H | $CH_3$ | H | H | ![3,4-dimethoxyphenyl-N(CH₂)₂NH-] | 4 | O | 2' | 7.5–6.5(m,1H);5.06(s,1H);4.1–3.9 (m,2H);3.81(s,6H);3.4–2.5(m,6H); 3.48(s,3H);2.4–1.8(m,4H). |
| 85 | H | H | $C_2H_5$ | H | H | ![3,4-dimethoxyphenyl-N(CH₂)₂N(CH₃)-] | 4 | O | 2' | 7.5–6.5(m,1H);5.05(s,1H);4.1–3.7 (m,4H);3.81(s,6H);3.4–2.5(m,6H); 2.4–1.8(m,4H);2.39(s,3H);1.3 (t,3H). |
| 86 | H | H | $C_2H_5$ | H | H | ![3,4,5-trimethoxyphenyl-(CH₂)₂-piperidinyl] | 4 | O | 2' | 7.4–6.4(m,10H);5.08(s,1H);4.1–3.7 (m,4H);3.86+3.81(2s,9H);3.4–2.5 (m,14H);2.4–1.8(m,4H);1.3(t,3H). |
| 87 | H | H | $n-C_3H_7$ | H | H | ![3,4,5-trimethoxyphenyl-(CH₂)₂-piperidinyl] | 4 | O | 2' | 7.4–6.4(m,10H);5.08(s,1H);4.1–3.7 (m,4H);3.86–3.81(2s,9H);3.4–2.5 (m,14H);2.4–1.8(m,6H);1.0(t,3H). |

-continued
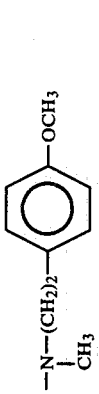
| Example No. | R$^1$ | R$^{1'}$ | R$^2$ | R$^3$ | R$^4$ | R$^6$ | m | X | Side chain in position | NMR (δ, ppm) |
|---|---|---|---|---|---|---|---|---|---|---|
| 88 | H | H | n-C$_3$C$_7$ | CH$_3$ | H | 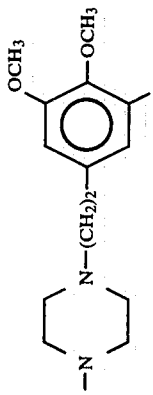 | 4 | O | 2' | 7.4–6.4(m,10H);4.1–3.7(m,4H);3.86+3.81(2s,9H);3.4–2.5(m,14H);2.4–1.8(m,6H);1.81(s,3H);1.0(t,3H). |
| 89 | H | H | C$_6$H$_5$ | H | H | | 4 | O | 2' | 7.4–6.5(m,17H);5.25(s,1H);4.2–3.9(m,2H);3.82(s,3H);3.3–2.5(m,6H); 2.4(s,3H);2.2–1.6(m,4H). |
| 90 | H | H | C$_6$H$_5$ | CH$_3$ | H | 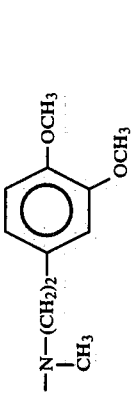 | 4 | O | 2' | 7.4–6.4(m,15H);4.2–3.9(m,2H);3.87+3.81(2s,9H);3.3–2.5(m,14H);2.1–1.6(m,4H);1.84(s,3H). |
| 91 | H | H | C$_6$H$_5$ | CH$_3$ | H | 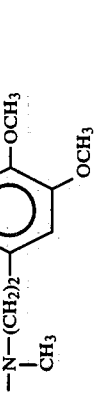 | 4 | O | 2' | 7.4–6.5(m,16H);4.2–3.9(m,2H);3.82(s,6H);3.3–2.5(m,6H);2.4(s,3H); 2.1–1.6(m,4H);1.85(s,3H). |

-continued
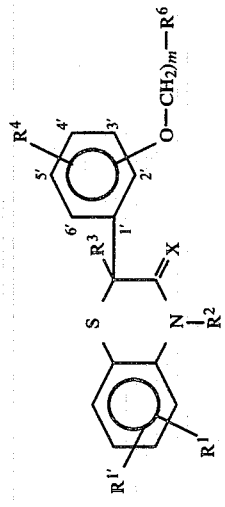
| Example No. | R$^1$ | R$^{1'}$ | R$^2$ | R$^3$ | R$^4$ | R$^6$ | m | X | Side chain in position | NMR (δ, ppm) |
|---|---|---|---|---|---|---|---|---|---|---|
| 92 | H | H | C$_6$H$_5$ | H | H | ![OCH3 OCH3 -N(CH2)2 H] | 4 | O | 2' | 7.4–6.5(m,16H);5.22(s,1H);4.2–3.9(m,2H);3.82(s,6H);3.3–2.5(m,6H);2.1–1.6(m,4H). |
| 93 | 6-OCH$_3$ | H | CH$_3$ | C$_2$H$_5$ | H | ![OCH3 OCH3 -N(CH2)2 CH3] | 4 | O | 2' | 7.4–6.5(m,10H);4.2–3.9(m,2H);3.81(s,9H);3.51(s,3H);3.4–2.5(m,6H);2.4(s,3H);2.2–1.6(m,6H);1.0(t,3H). |
| 94 | 6-F | H | C$_2$H$_5$ | H | H | ![OCH3 OCH3 -N(CH2)2 CH3] | 4 | O | 2' | 7.4–6.5(m,10H);5.05(s,1H);4.2–3.8(m,4H);3.81(s,6H);3.4–2.5(m,6H);2.4(s,3H);2.2–1.6(m,4H);1.25(t,3H). |
| 95 | 6-Cl | H | C$_6$H$_5$ | CH$_3$ | H | ![OCH3 OCH3 -N(CH2)2 CH3] | 4 | O | 2' | 7.4–6.5(m,15H);4.2–3.9(m,2H);3.82(s,6H);3.4–2.5(m,6H);2.4(s,3H);2.2–1.6(m,4H);1.81(s,3H). |
| 96 | 6-CH$_3$ | 7-CH$_3$ | CH$_3$ | H | H | ![OCH3 OCH3 -N-(piperidine)] | 4 | O | 2' | 7.4–6.5(m,9H);5.1(s,1H);4.2–3.9(m,2H);3.80(s,6H);3.4–2.5(m,14H);2.35(s,6H);2.3–1.7(m,4H). |

-continued
| Example No. | $R^1$ | $R^{1'}$ | $R^2$ | $R^3$ | $R^4$ | $R^6$ | m | X | Side chain in position | NMR (δ, ppm) |
|---|---|---|---|---|---|---|---|---|---|---|
| 97 | 6-$CH_3$ | H | $C_2H_5$ | $CH_3$ | H | 3,4-di-$OCH_3$-phenyl-$CH_2$-N($CH_3$)- | 4 | O | 2' | 7.4–6.5(m,10H);4.2–3.7(m,4H); 3.84(s,6H);3.4–2.5(m,6H);2.4 (s,3H);2.35(s,3H);1.79(s,3H);1.0(t,3H). |
| 98 | H | H | $CH_3$ | $CH_3$ | 4'-$OCH_3$ | 3,4-di-$OCH_3$-phenyl-$CH_2$-N($CH_3$)- | 4 | O | 2' | 7.4–6.5(m,10H);4.1–3.9(m,2H); 3.87+3.83(2s,9H);3.52(s,3H); 3.4–2.5(m,6H);2.4(s,3H);2.3–1.7 (m,4H);1.80(s,3H). |
| 99 | H | H | $CH_3$ | $CH_3$ | 6'-$OCH_3$ | 3,4-di-$OCH_3$-phenyl-$CH_2$-N($CH_3$)- | 4 | O | 2' | 7.4–6.5(m,10H);4.1–3.9(m,2H); 3.86+3.81(2s,9H);3.51(s,3H); 3.3–2.5(m,6H);2.48(s,3H);2.4–1.6 (m,4H);1.82(s,3H). |
| 100 | H | H | $CH_3$ | H | 4'-$OCH_3$ | 3,4,5-tri-$OCH_3$-phenyl-piperidinyl | 4 | O | 2' | 7.4–6.4(m,9H);5.05(s,1H);4.1–3.9 (m,2H);3.87+3.82(2s,12H);3.54(s, 3H);3.3–2.5(m,14H);2.4–1.6(m,4H). |

-continued

| Example No. | R[1] | R[1'] | R[2] | R[3] | R[4] | R[6] | m | X | Side chain in position | NMR (δ, ppm) |
|---|---|---|---|---|---|---|---|---|---|---|
| 101 | H | H | CH$_3$ | CH$_3$ | 5'-F | 3,4,5-tri-OCH$_3$-C$_6$H$_2$-N(piperazinyl)-(CH$_2$)$_2$- | 4 | O | 2' | 7.4–6.4(m,9H);4.1–3.9(m,2H);3.86+3.82(2s,9H);3.54(s,3H);3.3–2.5(m,14H);1.79(s,3H). |
| 102 | H | H | CH$_3$ | CH$_3$ | 5'-Cl | 3,4-di-OCH$_3$-C$_6$H$_3$-N(CH$_3$)-(CH$_2$)$_2$- | 4 | O | 2' | 7.4–6.5(m,10H);4.1–3.9(m,2H);3.82(s,6H);3.53(s,3H);3.3–2.6(m,6H);2.4(s,3H);2.3–1.6(m,4H);1.82(s,3H). |
| 103 | H | 7-CH$_3$ | CH$_3$ | H | 3'-Cl | 3,4-di-OCH$_3$-C$_6$H$_3$-N(CH$_3$)-(CH$_2$)$_2$- | 4 | O | 2' | 7.4–6.5(m,9H);5.08(s,1H);4.1–3.9(m,2H);3.82(s,6H);3.48(s,3H);3.3–2.6(m,6H);2.4(s,3H);2.4–1.6(m,4H). |
| 104 | H | H | CH$_3$ | H | 5'-CH$_3$ | 4-OCH$_3$-C$_6$H$_4$-N(CH$_3$)-(CH$_2$)$_2$- | 4 | O | 2' | 7.4–6.5(m,11H);5.07(s,1H);4.1–3.9(m,2H);3.81(s,3H);3.47(s,3H);3.3–2.6(m,6H);2.35(s,3H);2.31(s,3H);2.3–1.6(m,4H). |

-continued

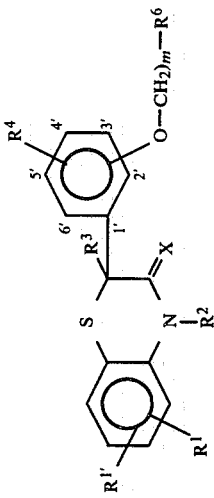

| Example No. | R¹ | R¹' | R² | R³ | R⁴ | R⁶ | m | X | Side chain in position | NMR (δ, ppm) |
|---|---|---|---|---|---|---|---|---|---|---|
| 105 | H | H | C₂H₅ | H | 5'-NHCOCH₃ | piperazine with 3,4,5-trimethoxyphenyl-N-(CH₂)₂- | 4 | O | 2' | 7.4–6.5(m,9H);6.2(br.s,1H);5.08(s,1H);4.1–3.6(m,4H);3.86+3.81(2s,9H);3.3–2.6(m,14H);2.4(s,3H);2.3–1.7(m,4H);1.2(t,3H). |
| 106 | H | H | CH₃ | CH₃ | 5'-OCH₃ | -N(CH₃)-CH(CH₃)-CH₂- with 3,4,5-trimethoxyphenyl | 4 | O | 2' | 7.4–6.5(m,9H);4.1–3.9(m,2H);3.9–3.8(3s,12H);3.51(s,3H);3.3–2.7(m,5H);2.4(s,3H);2.3–1.7(m,4H);1.82(s,3H);1.05(d,3H). |
| 107 | H | H | C₆H₅ | H | 5'-F | -N(CH₃)-(CH₂)₂- with 3,4-dimethoxyphenyl | 4 | O | 2' | 7.4–6.5(m,15H);5.25(s,1H);4.1–3.9(m,2H);3.82(s,6H);3.3–2.6(m,6H);2.4(s,3H);2.3–1.7(m,4H). |
| 108 | H | H | CH₃ | CH₃ | 4'-NO₂ | -N(CH₃)-(CH₂)₂- with 3,4-dimethoxyphenyl | 4 | O | 2' | 8.1–6.5(m,10H);4.1–3.9(m,2H);3.82(s,6H);3.54(s,3H);3.3–2.6(m,6H);2.4(s,3H);2.3–1.6(m,4H);1.84(s,3H). |

-continued

| Example No. | R¹ | R¹' | R² | R³ | R⁴ | R⁶ | m | X | Side chain in position | NMR (δ, ppm) |
|---|---|---|---|---|---|---|---|---|---|---|
| 109 | 6-F | H | CH₃ | CH₃ | 5'-OCH₃ | 4-(OCH₃), 3-(OCH₃)-C₆H₃-N(CH₃)-(CH₂)₂- | 4 | O | 2' | 7.4–6.5(m,9H);4.1–3.9(m,2H);3.82 (s,9H);3.51(s,3H);3.3–2.6(m,6H); 2.4(s,3H);2.3–1.6(m,4H);1.78(s, 3H). |
| 110 | 6-OCH₃ | H | CH₃ | H | 5'-F | 3,4,5-(OCH₃)₃-C₆H₂-piperazinyl- | 4 | O | 2' | 7.4–6.5(m,8H);5.10(s,1H);4.1–3.9. (m,2H);3.9–3.8(3s,12H);3.51(s, 3H);3.3–2.5(m,14H);2.3–1.6(m,4H). |
| 111 | H | H | C₆H₄—4-OCH₃ | H | H | 4-(OCH₃), 3-(OCH₃)-C₆H₃-N(CH₃)-(CH₂)₂- | 4 | O | 2' | 7.4–6.5(m,15H);5.30(s,1H);4.1–3.9 (m,2H);3.9–3.8(2s,9H);3.3–2.5(m, 6H);2.42(s,3H);2.3–1.6(m,4H). |
| 112 | H | H | (CH₃)₂—CH | H | H | 4-(OCH₃), 3-(OCH₃)-C₆H₃-N(CH₃)-(CH₂)₂- | 4 | O | 2' | 7.4–6.5(m,11H);5.12(s,1H);4.3–3.9 (m,3H);3.82(s,6H);3.3–2.5(m,6H); 2.4(s,3H);2.3–1.6(m,4H);1.08(d, 6H). |

-continued

| Example No. | R¹ | R¹' | R² | R³ | R⁴ | R⁶ | m | X | Side chain in position | NMR (δ, ppm) |
|---|---|---|---|---|---|---|---|---|---|---|
| 113 | H | H | C₆H₅CH₂ | H | H | piperidinyl-N-(CH₂)₂-(3,4-dimethoxyphenyl) | 4 | O | 2' | 7.4–6.5(m,16H);5.15(s,1H);5.0 (s,2H);4.1–3.9(m,2H);3.83(s,6H); 3.3–2.5(m,14H);2.3–1.6(m,4H). |
| 114 | H | H | C₆H₅—(CH₂)₂ | H | H | CH₃-N((CH₂)₂-(3,4-dimethoxyphenyl)) | 4 | O | 2' | 7.4–6.5(m,16H);5.12(s,1H);4.1–3.7 (m,4H);3.81(s,6H);3.3–2.5(m, 6H);2.4(s,3H);2.3–1.6(m,6H). |
| 115 | H | H | cyclopentyl | CH₃ | H | CH₃-N((CH₂)₂-(3,4-dimethoxyphenyl)) | 4 | O | 2' | 7.4–6.5(m,11H);4.4–3.8(m,3H);3.81 (s,6H);3.3–2.4(m,7H);2.4(s,3H); 2.3–1.5(m,12H),1.81(s,3H). |
| 116 | H | H | 3,4-dimethoxyphenyl | H | H | piperidinyl-N-(CH₂)₂-(3,4-dimethoxyphenyl) | 4 | O | 2' | 7.4–6.4(m,14H);5.30(s,1H);4.1–3.9 (m,2H);3.83(s,12H);3.3–2.6(m,14H); 2.3–1.5(m,4H). |
| 117 | H | H | cyclohexylmethyl | H | H | CH₃-N((CH₂)₂-(3,4-dimethoxyphenyl)) | 4 | O | 2' | 7.5–6.5(m,11H);5.08(s,1H);4.1–3.7 (m,4H);3.82(s,6H);3.3–2.4(m,7H); 2.45(s,3H);2.3–1.5(m,14H). |

-continued
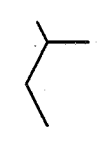
| Example No. | $R^1$ | $R^{1'}$ | $R^2$ | $R^3$ | $R^4$ | $R^6$ | m | X | Side chain in position | NMR (δ, ppm) |
|---|---|---|---|---|---|---|---|---|---|---|
| 118 | H | H | 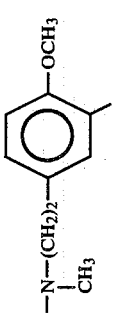 | H | H | 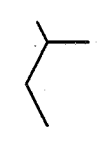 | 4 | O | 2' | 7.5–6.5(m,11H);5.05(s,1H);4.1–3.8 (m,3H);3.83(s,6H);3.3–2.5(m,6H); 2.4(s,3H);2.3–1.5(m,4H);1.05(d+t; 6H). |
| 119 | H | H | 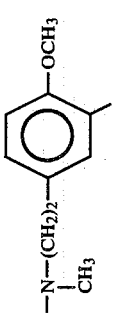 | H | H | 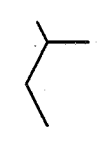 | 4 | O | 2' | 7.5–6.4(m,10H);5.00(s,1H);4.2–3.6 (m,4H);3.87+3.82(2s,9H);3.3–2.5 (m,15H);2.3–1.5(m,4H);1.05(d,6H). |
| 120 | H | H | 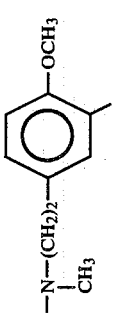 | H | H | 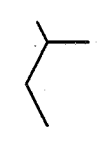 | 4 | O | 2' | 7.5–6.4(m,10H);5.02(s,1H);4.4–3.8 (m,3H);3.87+3.82(2s,9H);3.3–2.5 (m,14H). |
| 121 | H | H | 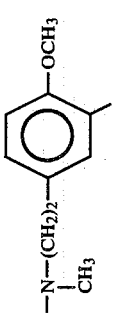 | H | H | 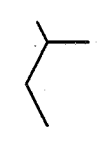 | 4 | O | 2' | 7.5–6.4(m,13H);5.2–5.0(3s,5H);4.1–3.9 4.1–3.9(m,2H);3.87+3.81(2s,9H); 3.3–2.5(m,14H);2.3–1.5(m,4H). |

-continued
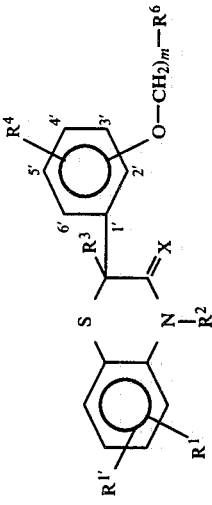
| Example No. | R[1] | R[1'] | R[2] | R[3] | R[4] | R[6] | m | X | Side chain in position | NMR (δ, ppm) |
|---|---|---|---|---|---|---|---|---|---|---|
| 122 | H | H | CH[3] | CH[2]=CHCH[2] | H | ![structure with OCH3, OCH3, -N-(CH2)2-CH3] | 4 | O | 2' | 7.5–6.4(m,11H);5.9–5.0(m,3H);4.1–3.9(m,2H);3.82(s,6H);3.51(s,3H); 3.3–2.5(m,8H);2.4(s,3H). |
| 123 | H | H | CH[3] | cyclopentyl | H | ![structure with OCH3, OCH3, -N-(CH2)2-CH3] | 4 | O | 2' | 7.5–6.4(m,11H);4.1–3.9(m,2H);3.83 (s,6H);3.48(s,3H);3.3–2.5(m,7H); 2.4(s,3H);2.3–1.7(m,12H). |
| 124 | H | H | CH[3] | C[6]H[5]CH[2] | H | ![structure with OCH3, OCH3, OCH3, -N-(CH2)2-piperidine] | 4 | O | 2' | 7.5–6.4(m,15H);4.1–3.9(m,2H);3.86+ 3.81(2s,9H);3.47(s,3H);3.3–2.5 (m,16H);2.3–1.7(m,4H). |
| 125 | H | H | CH[3] | isobutyl | H | ![structure with OCH3, OCH3, OCH3, -N-(CH2)2-piperidine] | 4 | O | 2' | 7.5–6.4(m,10H);4.1–3.8(m,2H);3.87+ 3.82(2s,9H);3.5(s,3H);3.3–2.5(m, 15H);2.3–1.7(m,4H);1.1(d+t,6H). |

-continued

Structure:

R¹'—[phenyl with R¹]—S—C(R³)(—[phenyl 1'-6' with R⁴ at 4', O—(CH₂)ₘ—R⁶ at 2'])—C(=X)—N(R²)

| Example No. | R¹ | R¹' | R² | R³ | R⁴ | R⁶ | m | X | Side chain in position | NMR (δ, ppm) |
|---|---|---|---|---|---|---|---|---|---|---|
| 126 | H | H | H | H | H | piperidin-1-yl-N—(CH₂)₂—N< attached to 3,4,5-tri-OCH₃-phenyl (—N(piperidine)—(CH₂)₂—N(aryl) where aryl = 3,4,5-trimethoxyphenyl) | 4 | O | 2' | 7.4–6.4(m,11H);5.0(s,1H);4.1–3.9(m,2H);3.3–2.6(m,14H);2.4–1.5(m,4H) |
| 127 | H | H | CH₃ | C₆H₅CH₂CH₂ | H | —N(CH₃)—(CH₂)₂—N(aryl) where aryl = 3,4-dimethoxyphenyl | 4 | O | 2' | 7.4–6.5(m,16H);4.1–3.9(m,2H);3.82(s,6H);3.50(s,3H);3.3–2.4(m,8H);2.35(s,3H);2.2–1.6(m,6H). |

EXAMPLE 128

(−)-2,3-Dihydro-2,4-dimethyl-2-[2-[4-[4-[2-(3,4,5-trimethoxyphenyl)ethyl]piperazinyl]butoxy]phenyl]-benzothiazin-3-one dihydrochloride

(a)
2,3-Dihydro-2,4-dimethyl-2-(3-ethoxycarbonyl)propoxyphenylbenzothiazin-3-one 4.4 g (90.5 mmol) of sodium hydride are suspended in 200 ml of absolute DMF. After addition of 17.2 g (60.3 mmol) of the compound from Example (1e), the mixture is stirred for 30 min and then, at 0° C., 10.3 ml (66.4 mmol) of ethyl 4-bromobutyrate are added. After stirring at room temperature for 7 hours, the mixture is poured onto water and extracted with methylene chloride. The organic phase is washed four times with water, dried with sodium sulfate and concentrated. Chromatography on 1 kg of silica gel using ethyl acetate/cyclohexane (1:3) as the mobile phase provides 19.4 g of colorless oil.

$^1$H-NMR(CDCl$_3$): δ = 1.15 (t,3H); 1.75 (s,3H); 1.9–3.0 (m, 4H); 3.35 (s,3H); 3.9 (q,2H); 4.1 (t,2H); 6.4–7.4 (m,8H) ppm.

(b)
2,3-Dihydro-2,4-dimethyl-2-(3-carboxypropoxy)-phenylbenzothiazin-3-one 36.3 ml of 2N NaOH are added to 19.4 g (48 mmol) of the compound from Example (128a), and the mixture is diluted with ethanol until a clear solution is obtained. The solution is stirred at room temperature for 2.5 hours, and the ethanol is evaporated off, and the residue is acidified with 2N HCl. Extraction with ethyl acetate, drying with sodium sulfate, and concentration provides 16.2 g of colorless crystals.

(c)
(−)-2,3-Dihydro-2,4-dimethyl-2-(3-carboxypropoxy)-phenylbenzothiazin-3-one 9 g (24.2 mmol) of the racemic carboxylic acid and 10.4 g (24.2 mmol) of brucine are dissolved in about 50 ml of acetone. Water is added until the solution just starts to become cloudy, and the solution is allowed to stand overnight and is then filtered with suction. The resulting salt is recrystallized from acetone/water until its specific rotation is −158 degrees (c=0.99, methanol). 4.1 g of this salt are dissolved in 60 ml of hot water, and 7 ml of 1N KOH are added. After 3 hours, the precipitated brucine is filtered off with suction, and the filtrate is acidified with 5N HCl, extracted with methylene chloride, and the organic phase is dried with magnesium sulfate and concentrated. After trituration with isopropyl ether, 2.05 g of colorless crystals are obtained, specific rotation $[α]_D^{20} = -245$ degrees (c=1, methanol).

(d)
(−)-2,3-Dihydro-2,4-dimethyl-2-|2-(4-hydroxy)butoxyl|-phenylbenzothiazin-3-one 2.05 g (5.5 mmol) of the compound from Example (128c), together with 0.71 g (7 mmol) of triethylamine, are dissolved in 5 ml of toluene. A solution of 0.66 g (7 mmol) of methyl chloroformate in 30 ml of ether is added dropwise, and then the solution is heated to reflux for 4 hours, filtered hot and concentrated. The residue is dissolved in 10 ml of THF, and the solution is added dropwise to a suspension of 0.6 g of sodium borohydride in 10 ml of absolute THF. After stirring at room temperature for 12 hours, the mixture is acidified with 1N HCl, the THF is removed in vacuo, and the residue is taken up in ethyl acetate/water, extracted with ethyl acetate, and the organic solution is washed with saturated sodium chloride solution and dried over magnesium sulfate. After concentration, the residue is chromatographed on silica gel using ethyl acetate/cyclohexane (1:1). 0.7 g of colorless crystals of melting point 88°–91° C. are obtained $[α]_D^{20} = -302$ degrees (c=1, methanol).

(e)
(−)-2,3-Dihydro-2,4-dimethyl-2-[2-(4-methanesulfonyloxybutoxy]phenylbenzothiazin-3-one 0.7 g (1.96 mmol) of the compound from Example (128d) is initially introduced together with 0.3 g (0.275 mmol) of triethylamine in 10 ml of THF. At 0° C., 0.22 g (1.96 mmol) of methanesulfonyl chloride is added dropwise. After 4 hours at room temperature, the mixture is poured onto 1N HCl, extracted with ethyl acetate, and the organic phase is dried with magnesium sulfate and concentrated. 1.05 g of colorless oil is obtained.

$^1$H-NMR(CDCl$_3$): δ = 1.2 (t,3H); 1.77 (s,3H); 1.7–2.2 (m,4H); 2.9 (s,3H); 3.38 (s,3H); 3.8–4.4 (m,4H); 6.4–7.3 (m,8H) ppm.

(f)
(−)-2,3-Dihydro-2,4-dimethyl-2-[2-[4-[4-[2-(3,4,5-trimethoxyphenyl)ethyl]piperazinyl]butoxy]phenyl]-benzothiazin-3-one dihydrochloride 1.05 g of the mesylate from Example (128e), together with 0.63 g of 2-(3,4,5-trimethoxyphenyl)ethylpiperazine, 0.5 g of potassium carbonate and 0.4 g of sodium iodide, in 20 ml of isopropanol are heated to reflux for 9 hours. After cooling, the mixture is filtered off with suction, and the filtrate is concentrated. Chromatography on silica gel using methylene chloride methanol (9:1) as the mobile phase provides 0.68 g of colorless oil, $[α]_D^{20} = -114.5$ degrees (c=0.496, methanol).

To convert into the hydrochloride, the product is taken up in acetone, and the solution is acidified with 2.5N ethanolic HCl, concentrated, and the residue is taken up in acetone and filtered off with suction. 0.7 g of colorless crystals are obtained, melting point 241°–244° C. (decomposition), $[α]_D^{20} = -130$ degrees (c=0.4, methanol).

EXAMPLE 129

(+)-2,3-Dihydro-2,4-dimethyl-2-[2-[4-[4-[2-(3,4,5-trimethoxyphenyl)ethyl]piperazinyl]butoxy]phenyl]-benzothiazin-3-one dihydrochloride

(a)
2,3-Dihydro-2,4-dimethyl-2-(2-hydroxyphenyl)benzothiazin-3-one (1S)-bornan-2-one-1-carboxylate 5.3 g (25.7 mmol) of (1S)-bornan-2-one-1-carbonyl chloride are added to 5 g (17.5 mmol) of the compound from Example (1e) dissolved in 70 ml of pyridine. After addition of 1 g of 4-dimethylaminopyridine, the mixture is stirred at room temperature for 48 hours. The solution is poured onto 1 l of saturated oxalic acid solution, and the mixture is extracted with ethyl acetate (3×). The combined organic phases are washed with saturated NaCl solution, dried over sodium sulfate and concentrated. The isomers are separated on 1 kg of silica gel using ethyl acetate/cyclohexane (1:4).

Isomer 1

Rf=0.18

Melting point 178°–181° C., $[\alpha]_D^{20} = +299$ degrees (c=0.98, CH$_2$Cl$_2$) 2.8 g Isomer 2

Rf=0.15

Melting point 159° C.

$[\alpha]_D^{20} = -302.5$ degrees (c=1.026, CH$_2$Cl$_2$) 2.2 g (b)
(+)-2,3-Dihydro-2,4-dimethyl-2-(2-hydroxyphenyl)-benzothiazin-3-one 0.5 g of sodium hydride are dissolved in 40 ml of methanol, and 2 g (4.45 mmol) of isomer 1 from Example 129a are added. After refluxing for 3 hours, the mixture is poured onto 200 ml of 1N HCl, then extracted 3× with ethyl acetate, and the organic phase is washed with saturated NaCl solution, dried with MgSO$_4$ and concentrated. Crystallization from ethyl acetate provides 1.25 g of colorless crystals of melting point 182°–184° C., $[\alpha]_D^{20} = +351$ degrees (c=0.62, CH$_2$Cl$_2$).

(c)
(+)-2,3-Dihydro-2,4-dimethyl-2-[2-(4-bromobutoxy)-phenyl]benzothiazin-3-one 1.25 g of the compound from Example (129b), together with 2.85 g of 1,4-dibromobutane and 1.4 g of potassium carbonate, in 50 ml of 2-butanone are heated to reflux for 3 hours. After filtration, the filtrate is concentrated and the excess dibromobutane is removed under high vacuum.

(d)(+)-2,3-Dihydro-2,4-dimethyl-2-[2-[4-[4-[2-(3,4,5-trimethoxyphenyl)ethyl]piperazinyl]butoxy]phenyl]-benzothiazin-3-one dihydrochloride 1.85 g of the compound from Example (129c) are reacted with 2.0 g of 2-(3,4,5-trimethoxyphenyl)ethylpiperazine by the process indicated in Example (128f). 1.55 g of colorless crystals of the title compound are obtained, melting point 237°–240° C., $[\alpha]_D^{20} = +119.5$ degrees (c=0.41, methanol).

EXAMPLE 130

2,3-Dihydro-2-ethyl-4-methyl-2-[2-[4-[4-[2-(3,4,5-trimethoxyphenyl)ethyl]piperazinyl]butoxy]phenyl]benzothiazin-3-one dihydrochloride (a)
2,3-Dihydro-2-ethyl-4-methyl-2-(2-methoxyphenyl)-benzothiazin-3-one 0.35 g of sodium hydride (50% in oil) is washed 2× with hexane and suspended in 10 ml of DMF. 1.55 g of the compound from Example (3a) are added, and the mixture is stirred for 20 min. Then, at room temperature, 1.27 g of ethyl iodide are added dropwise. After 3 hours, the solution is poured onto water, and the mixture is extracted 3× with ethyl acetate, and the combined organic phases are washed 5× with water, dried with magnesium sulfate and concentrated. Trituration with isopropyl ether provides 1.35 g of crystals of melting point 98° C.

(b)
2,3-Dihydro-2-ethyl-4-methyl-2-(2-hydroxyphenyl)-benzothiazin-3-one 1.35 g (4.3 mmol) of the compound from Example (130a) are reacted with boron tribromide by the process described in Example (1e). 1.1 g of colorless crystals of melting point 165°–168° C. are obtained.

(c)
2,3-Dihydro-2-ethyl-4-methyl-2-[2-[4-[4-[2-(3,4,5-trimethoxyphenyl)ethyl]piperazinyl]butoxy]phenyl]benzothiazin-3-one dihydrochloride 1.1 g of the compound from Example (130b) are reacted with 2.38 g of 1,4-dibromobutane by the process described in Example (3c). 1.66 g of the bromide is obtained, and this is reacted further without purification. 0.83 g (1.91 mmol) are reacted with 0.8 g of 2-(3,4,5-trimethoxyphenyl)ethylpiperazine and 0.7 g of potassium carbonate by the process described in Example (129f). 0.75 g of colorless crystals of melting point 220°–223° C. are obtained.

EXAMPLE 131

2,3-Dihydro-2-ethyl-4-methyl-2-[2-[4-[4-[2-(3,5-dimethoxyphenyl)ethyl]piperazinyl]butoxy]phenyl]benzothiazin-3-one dihydrochloride 0.83 g of the compound from Example (130b) are reacted, in analogy to the procedure indicated in Example (130c), first with 1,4-dibromobutane and then with 0.72 g (2.87 mmol) of 2-(3,5-dimethoxyphenyl)ethylpiperazine. 0.43 g of colorless crystals of melting point 216°–218° C. are obtained.

EXAMPLE 132

2,3-Dihydro-2-isopropyl-4-methyl-2-[2-[4-[4-[2-(3,4,5-trimethoxyphenyl)ethyl]piperazinyl]butoxy]phenyl]-benzothiazin-3-one dihydrochloride (a)
2,3-Dihydro-2-isopropyl-4-methyl-2-(2-methoxyphenyl)-benzothiazin-3-one 0.35 g (7.6 mmol) of NaH (50% in oil) are washed 2× with hexane, suspended in DMF (15 ml), and 1.55 g of 2,3-dihydro-4-methyl-2-(2-methoxyphenyl)benzothiazin-3-one are added. After 30 min. at room temperature, 1.29 g (7.6 mmol) of 2-iodopropane are added, and the mixture is stirred for a further 3 hours. It is partitioned between ethyl acetate and water, and the organic phase is washed 5× with water and with saturated NaCl solution and dried with MgSO$_4$. The title compound crystallizes on trituration with isopropyl ether.

Melting point 121° C.

(b)
2,3-Dihydro-2-isopropyl-4-methyl-2-(2-hydroxyphenyl)-benzothiazin-3-one 1.35 g of the compound from Example (132a) are dissolved in 20 ml of methylene chloride, and 5 ml of boron tribromide solution in hexane (1M) are added dropwise. After stirring for 3 hours, the mixture is poured onto 150 ml of water, and this is extracted with CH$_2$Cl$_2$ and dried over MgSO$_4$. After concentration, the residue is recrystallized from ethyl acetate. 0.75 g of colorless crystals of melting point 189°–192° C. are obtained.

(c)
2,3-Dihydro-2-isopropyl-4-methyl-2-[2-(4-bromobutoxy)-phenyl]benzothiazin-3-one 0.83 g of the compound from Example (132b) is heated together with 1.72 g of 1,4-dibromobutane and 1 g of potassium carbonate in 20 ml of methyl ether ketone to reflux for 4 hours. After filtration, the filtrate is concentrated and recrystallized from isopropyl ether. 1.19 g of colorless crystals of melting point 84°–87° C. are obtained.

(d)
2,3-Dihydro-2-isopropyl-4-methyl-2-[2-[4-[4-[2-(3,4,5-trimethoxyphenyl)ethyl]piperazinyl]butoxy]phenyl]-benzothiazin-3-one dihydrochloride Prepared from 1.19 g of the compound from Example (132c) and 1 g of 2-(3,4,5-trimethoxyphenyl)ethylpiperazine in analogy to the procedure indicated in Example (128f). 0.75 g of colorless crystals of melting point 235°–238° C. are obtained.

EXAMPLE 133

2,3-Dihydro-2,4-dimethyl-2-[3-methoxy-2-[4-[4-[2-(3,4,5-trimethoxyphenyl)ethyl]piperazinyl]butoxy]-phenyl]benzothiazin-3-one dihydrochloride

(a) 2-Benzyloxy-3-methoxybenzaldehyde 50 g (0.3 mole) of 3-methoxysalicylaldehyde are heated to reflux for 3 hours with 51.3 g (0.3 mole) of benzyl bromide and 48.4 g of potassium carbonate in 300 ml of acetone. After filtration, the filtrate is concentrated. 71.8 g of the title compound are obtained as a yellow oil.

$^1$H-NMR(CDCl$_3$): δ=3.78 (s,3H); 5.04 (s,2H); 6.5–7.3 (m,3H); 7.17 (s,5H); 10.0 (s,1H) ppm.

(b) 2-Benzyloxy-3-methoxybenzaldehyde cyanohydrin 71.8 g of the compound from Example (133a) are heated on a steambath with 125 ml of saturated sodium bisulfite solution and 15 ml of ethanol. 200 ml of ethanol and 200 ml of isopropyl ether are added to the solution, and the mixture is stirred for 3 hours. The precipitated bisulfite adduct is filtered off with suction and dried in air. After taking it up in 200 ml of water, 32.5 g of potassium cyanide in 125 ml of H$_2$O are added dropwise at 0° C., with stirring. After 2 hours, the solid is filtered off with suction, washed with water and recrystallized from ethyl acetate/hexane. 51 g of colorless crystals of melting point 89°–91° C. are obtained.

(c) Ethyl 2-benzyloxy-3-methoxymandelate 5 ml of absolute ethanol and 50 ml of saturated ethereal HCl are added to 5 g of the compound from Example (133b), and the mixture is allowed to stand at 5° C. for 24 hours. Water is added to the yellow solution, the mixture is stirred for 1 hour, and the ether phase is separated off, dried with MgSO$_4$ and concentrated. Chromatography on silica gel using ethyl acetate/cyclohexane (1:4) as the mobile phase provides 3.75 g of the title compound as an oil.

$^1$H-NMR(CDCl$_3$): δ=1.05 (t,3H); 3.7 (s,3H); 4.05 (q,3H); 4.95 (s,2H); 5.3 (s,1H); 6.6–6.9 (m, 3H); 7.0–7.5 (m,5H) ppm.

(d) Ethyl 2-benzyloxy-3-methoxy-O-methanesulfonylmandelate 3.75 g of the compound from Example (133c) are dissolved together with 3.5 ml of triethylamine in 20 ml of CH$_2$Cl$_2$. At −10° C., 1.1 ml of methanesulfonyl chloride is added dropwise. After warming to room temperature, the mixture is stirred for a further 90 min, and poured onto 2N HCl, and the phases are separated and the aqueous phase is again extracted with methylene chloride. After drying with MgSO$_4$, the organic phase is concentrated. 4.7 g of the title compound are obtained as an oil.

$^1$H-NMR(CDCl$_3$): δ=1.1 (t,3H); 2.9 (s,3H); 3.75 (s,3H); 4.1 (q,2H); 5.0 (s,2H); 6.17 (s,1H); 6.88 (s,3H); 7.0–7.4 (m,5H) ppm.

(e) 2,3-Dihydro-2-(2-benzyloxy-3-methoxyphenyl)benzothiazin-3-one 4.7 g of the mesylate from Example (133d) and 1.53 g of 2-aminothiophenol and 30 ml of DMF are stirred at room temperature for 18 hours and at 80° C. for 2 hours, then poured onto 200 ml of 1N HCl, the mixture is extracted with ethyl acetate, and the organic phase is washed with water, dried with MgSO$_4$ and concentrated. The title compound crystallizes from ethyl acetate/ether, 1.9 g, melting point 151°–153° C.

(f) 2,3-Dihydro-2,4-dimethyl-2-(2-benzyloxy-3-methoxyphenyl)benzothiazin-3-one 1.9 g of the compound from Example (133e) are added to 0.8 g of NaH which has been washed with hexane and is suspended in 15 ml of DMF. After stirring for 30 min, 1.25 ml of iodomethane is added, and the mixture is stirred for 2 hours and then poured onto 1N HCl. Extraction with ethyl acetate, washing of the organic phase with H$_2$O and dryng with MgSO$_4$ provides 1.95 g of the title compound as a yellow oil.

(g) 2,3-Dihydro-2,4-dimethyl-2-(2-hydroxy-3-methoxyphenyl)-benzothiazin-3-one 1.95 g of the compound from Example (133f) in 20 ml of ethanol and 3 ml of 2.5N ethanolic HCl are hydrogenated with Pd/C under a pressure of 1 bar of H$_2$. Chromatography on silica gel using ethyl acetate/cyclohexane (1:2) as the mobile phase provides 0.35 g of the title compound of melting point 153° C.

(h) 2,3-Dihydro-2,4-dimethyl-2-[3-methoxy-2-[4-[4-[2-(3,4,5-trimethoxphenyl)ethyl]piperazinyl]butoxy]-phenyl]-benzothiazin-3-one dihydrochloride 0.35 g of the compound from Example (133g) are reacted in analogy to the process indicated in Example (130c) first with 0.48 g of 1,4-dibromobutane and then with 0.84 g of 2-(3,4,5-trimethoxyphenyl)ethylpiperazine. 0.6 g of the title compound is obtained as colorless crystals of melting point 183°–185° C.

EXAMPLE 134

2,3-Dihydro-2,4-dimethyl-2-[4-methoxy-2-[4-[4-[2-(3,4,5-trimethoxyphenyl)ethyl]piperazinyl]butoxy]-phenyl]-benzothiazin-3-one dihydrochloride Prepared from 4-methoxysalicylaldehyde in analogy to the procedures indicated in Example (133a)–(h).

$^1$H-NMR (free base, CDCl$_3$): δ=1.5–2.0 (m,7H); 2.3–2.9 (m,14H); 3.5 (s,3H); 3.7 (s,3H); 3.8 (s,6H); 3.9 (t,3H); 6.4 (s,2h); 6.5–7.4 (m, 9H) pm.

EXAMPLE 135

2,3-Dihydro-2,4-dimethyl-2-[5-methoxy-2-[4-[4-[2-(3,4,5-trimethoxyphenyl)ethyl]piperazinyl]butoxy]benzothiazin-3-one dihydrochloride Prepared from 5-methoxysalicylaldehyde by the procedures indicated in Examples (133a)–(h), melting point 216° C.

$^1$H-NMR (free base, CDCl$_3$): δ=1.5–2.0 (m,7H); 2.3–2.9 (m,14H); 3.58 (s,3H); 3.67 (s,3H); 3.8 (s,6H); 3.9 (t,3H); 6.4 (s,2H); 6.5–7.4 (m,9H) ppm.

EXAMPLE 136

2,3-Dihydro-2,4-dimethyl-2-[5-chloro-2-[4-[4-[2-(3,4,5-trimethoxyphenyl)ethyl]piperazinyl]butoxy]phenyl]-benzothiazin-3-one dihydrochloride

(a) 5-Chlorosalicylaldehyde 64.25 g (0.5 mole) of p-chlorophenol and 55 g (0.2 mole) of trioctylamine are dissolved in 100 ml of toluene. Under N$_2$, 13 g of tin tetrachloride are added dropwise at 0° C. After 20 min at room temperature, 33 g of dried paraformaldehyde are added, and the mixture is heated at 100° C. for 5 hours. After cooling, the mixture is poured onto 2.5 l of H$_2$O, and the mixture is acidified to pH 2 with 2N HCl and extracted with diethyl ether. The ether phase is washed with saturated NaCl solution and dried with Na$_2$SO$_4$ and concentrated. Chromatography on silica gel using ethyl acetate/cyclohexane (1:6) provides 24 g of the title compound, melting point 99° C.

(b) 5-Chloro-2-methoxybenzaldehyde 4.3 g of 5-chlorosalicylaldehyde, together with 7.8 g of methyl iodide and 5.7 g of potassium carbonate, in 100 ml of acetone are heated to reflux (1 hour). After filtration, the filtrate is concentrated. 4.6 g of the title compound are obtained as an oil.

(c) Methyl 5-chloro-2-methoxymandelate

Prepared from 4.6 g of 5-chloro-2-methoxybenzaldehyde by the procedure indicated in Example (1a), yield 2.8 g of colorless oil.

$^1$H-NMR(CDCl$_3$): δ=3.64 (s,3H); 3.74 (s,3H); 5.22 (s,1H); 6.6–7.2 (m,3H) ppm.

(d) Methyl 5-chloro-2-methoxy-O-methanesulfonylmandelate

Prepared from 2.8 g of the compound from Example (136c) by the procedure indicated in Example (133d), by reaction with 1.37 g of methanesulfonyl chloride. 3.4 g of the title compound are obtained as an oil.

$^1$H-NMR(CDCl$_3$): δ=3.08 (s,3H); 3.7 (s,3H); 3.78 (s,3H); 6.1 (s,1H); 6.6–7.3 (m,3H) ppm.

(e) 2,3-Dihydro-2-(5-chloro-2-methoxyphenyl)benzothiazin-3-one

Prepared from 3.4 g of the compound from Example (136d) and 1.56 g of 2-aminothiophenol by the process described in Example (133e). 2.5 g of the title compound are obtained as pale yellow crystals.

(f) 2,3-Dihydro-2,4-dimethyl-2-(5-chloro-2-methoxyphenyl)-benzothiazin-3-one Prepared from 2.5 g of the compound from Example (136e) by alkylation with 1.5 ml of iodomethane by the procedure indicated in Example (1d). 2.33 g of colorless crystals of melting point 96° C. are obtained.

(g) 2,3-Dihydro-2,4-dimethyl-2-(5-chloro-2-hydroxyphenyl)-benzothiazin-3-one Prepared from 2.33 g of the compound from Example (136e) by the procedure indicated in Example (1d). 2.1 g of the title compound are obtained as colorless crystals melting point 211° C.

(h) 2,3-Dihydro-2,4-dimethyl-2-[2-(4-bromobutoxy)-5-chlorophenyl]benzothiazin-3-one Prepared from 2.1 g of the compound from Example (136g) and 3.8 ml of 1,4-dibromobutane by the procedure indicated in Example (3c). 2.9 g of the title compound are obtained as a yellowish oil.

(i) 2,3-Dihydro-2,4-dimethyl-2-[5-chloro-2-[4-[4-[2-(3,4,5-trimethoxyphenyl)ethyl]piperazinyl]butoxy]phenyl]-benzothiazin-3-one dihydrochloride Prepared from 1.5 g of the compound from Example (136h) and 1.01 g of 2-(3,4,5-trimethoxyphenyl)ethylpiperazine by the process described in Example (129d). 1.37 g of colorless crystals of melting point 246° C. are obtained.

EXAMPLE 137

2,3-Dihydro-2,4-dimethyl-2-[5-chloro-2-[4-[4-[2-(3,5-dimethoxyphenyl)ethyl]piperazinyl]butoxy]phenyl]benzothiazin-3-one dihydrochloride Prepared from 1.4 g of the compound from Example (136h) and 0.9 g of 2-(3,5-dimethoxyphenyl)ethylpiperazine by the procedure indicated in Example (129d). 0.9 g of colorless crystals of melting point 208° C. are obtained.

EXAMPLE 138

2,3-Dihydro-2,4-dimethyl-2-[5-methyl-2-[4-[4-[2-(3,4,5-trimethoxyphenyl)ethyl]piperazinyl]butoxy]phenyl]-benzothiazin-3-one dihydrochloride Prepared from p-cresol and the appropriate reagents in analogy to the procedures indicated in Example (136a)–(j). The title compound is obtained as colorless crystals of melting point 238° C. (decomposition).

EXAMPLE 139

2,3-Dihydro-2,4-dimethyl-2-[5-methyl-2-[4-[4-[2-(3,5-dimethoxyphenyl)ethyl]piperazinyl]butoxy]phenyl]-benzothiazin-3-one dihydrochloride Prepared from p-cresol and the appropriate reagents in analogy to the processes described in Example (136a)–(h) and 137. The title compound is obtained as colorless crystals of melting point 228° C.

EXAMPLE 140

2,3-Dihydro-2,4-dimethyl-2-[5-fluoro-2-[4-[4-[2-(3,4,5-trimethoxyphenyl)ethyl]piperazinyl]butoxy]pheny]benzothiazin-3-one dihydrochloride Prepared from 4-fluorophenol in analogy to the procedures indicated in Example (136a)–(i).

EXAMPLE 141

2,3-Dihydro-2,4-dimethyl-2-[2-[4-[4-[2-(3,5-dimethoxyphenyl)-ethyl]piperazinyl]butoxy]phenyl]benzothiazin-3-one dihydrochloride Prepared from 1.5 g (3.7 mmol) of 2,3-dihydro-2,4-dimethyl-2-[2-(4-bromobutoxy)phenyl]benzothiazin-3-one and 1.1 g of 2-(3,5-dimethoxyphenyl)ethylpiperazine by the process described in Example (129d). 0.9 g of colorless crystals of melting point 234° C. are obtained.

EXAMPLE 142

(+)-2,3-Dihydro-2-ethyl-4-methyl-2-[2-[4-[4-[2-(3,4,5-trimethoxyphenyl)ethyl]piperazinyl]butoxy]phenyl]-benzothiazin-3-one dihydrochloride (a)

2,3-Dihydro-2-ethyl-4-methyl-2-(2-hydroxyphenyl)benzothiazin-3-one (1S)-bornan-2-one-1-carboxylate Prepared by the procedure indicated in Example (129a) from 15.2 g of the compound from Example (130b) and 14 g of (1S)-bornan-2-one-1-carboxyl chloride. After chromatography on silica gel using ethyl acetate/cyclohexane (1:6) as the mobile phase, the following are obtained:

Isomer 1 colorless crystals, melting point 197° C., $[\alpha]_D^{20} = +280$ degrees (c=1, $CH_2Cl_2$) 7.1 g Isomer 2 colorless crystals, melting point 144° C. $[\alpha]_D^{20} = -264$ degrees (c=1, $CH_2Cl_2$) 6.9 g (b)(+)-2,3-Dihydro-2-ethyl-4-methyl-2-(2-hydroxyphenyl)-benzothiazin-3-one Prepared from isomer 1 of Example (142a) by the procedure indicated in Example (129b). 3.8 g of colorless crystals of melting point 187° C. are obtained, $[\alpha]_D^{20} = +270.6$ degrees (c=1, $CH_2Cl_2$).

(c)

(+)-2,3-Dihydro-2-ethyl-4-methyl-2-[2-[4-[4-[2-(3,4,5-trimethoxyphenyl)ethyl]piperazinyl]butoxy]phenyl]-benzothiazin-3-one dihydrochloride Prepared from 3.8 g of the compound from Example (142b) and 7.2 g of 2-(3,4,5-trimethoxyphenyl)ethylpiperazine by the procedure indicated in Example (129c). 2.8 g of colorless crystals of melting point 234° C. are obtained, $[\alpha]_D^{20} = +131$ degrees (c=1, $CH_2Cl_2$).

EXAMPLE 143

(−)-2,3-Dihydro-2-ethyl-4-methyl-2-[2-[4-4-[2-(3,4,5-trimethoxyphenyl)ethyl]piperazinyl]butoxy]phenyl]-benzothiazin-3-one dihydrochloride Prepared by the procedures of Example (142b) and (c) from isomer 2 of Example (142a). 2.4 g of colorless crystals of melting point 239° C. are obtained; $[\alpha]_D^{20} = -142.3$ degrees (c=1, $CH_2Cl_2$).

EXAMPLE 144

(+)-2,3-Dihydro-2-isopropyl-4-methyl-2-[2-[4-[4-[2-(3,4,5-trimethoxyphenyl)ethyl]piperazinyl]butoxy]-phenyl]benzothiazin-3-one dihydrochloride (a)

2,3-Dihydro-2-isopropyl-4-methyl-2-(2-hydroxyphenyl)-benzothiazin-3-one (1S)-bornan-2-one-1-carboxylate Prepared by the procedure indicated in Example (129a) from 14.7 g of the compound from Example (132b) and 13 g of (1S)-bornan-2-one-1-carbonyl chloride. After chromatography on silica gel using ethyl acetate/cyclohexane (1:6) as the mobile phase, the following are obtained Isomer 1 colorless crystals, melting point 196° C. $[\alpha]_D^{20} = +241$ degrees (c=1, $CH_2Cl_2$) 7.9 g Isomer 2 colorless crystals, melting point 160° C. $[\alpha]_D^{20} = -213$ degrees (c=1, $CH_2Cl_2$) 5.5 g (b)

(+)-2,3-Dihydro-2-isopropyl-4-methyl-2-(2-hydroxyphenyl)benzothiazin-3-one

Prepared from isomer 1 of Example (144a) by the procedure indicated in Example (129b). 3.6 g of colorless crystals of melting point 146° C. are obtained, $[\alpha]_D^{20} = +128$ degrees (c=1, $CH_2Cl_2$).

(c)

(+)-2,3-Dihydro-2-isopropyl-4-methyl-2-[2-[4-[4-(3,4,5-trimethoxyphenyl)ethyl]piperazinyl]butoxy]phenyl]-benzothiazin-3-one dihydrochloride Prepared from 5.1 g of the compound from Example (144b) and 5.0 g of 2-(3,4,5-trimethoxyphenyl)ethylpiperazine by the procedure indicated in Example (129c). 3.2 g of colorless crystals of melting point 240° C. are obtained, $[\alpha]_D^{20} = +115.3$ degrees (c=1, $CH_2Cl_2$).

EXAMPLE 145

(−)-2,3-Dihydro-2-isopropyl-4-methyl-2-[2-[4-[4-[2-(3,4,5-trimethoxyphenyl)ethyl]piperazinyl]butoxy]-phenyl]benzothiazin-3-one dihydrochloride Prepared from isomer 2 of Example (144a) by the procedures of Example (144b) and (c). 1.9 g of colorless crystals of melting point 242° C. are obtained; $[\alpha]_D^{20} = -120.1$ degrees (c=1, $CH_2Cl_2$).

We claim:

1. A benzothiazine derivative of the formula I

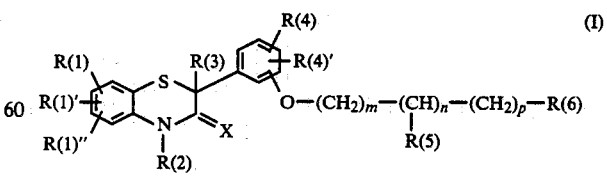

in which
R(1), R(1)' and R(1)" are identical or different and are independent of one another, and are hydrogen, $(C_1-C_4)$-alkyl, $(C_1-C_3)$-alkoxy, halogen, nitro, hydroxyl, acetamido or amino, R(2) is hydrogen, $(C_1-C_{10})$-alkyl, straight-chain or branched, $(C_3-C_{10})$-alkenyl, straight-chain or branched, phenyl or phenyl-$(C_1-C_4)$-alkyl, the phenyl ring in each case being unsubstituted or substituted by one, two or three substituents from the group consisting of $(C_1-C_4)$-alkyl, $(C_1-C_3)$-alkoxy, halogen, $(C_1-C_2)$-alkylenedioxy and nitro; $(C_4-C_8)$-cycloalkyl-$(C_1-C_4)$-alkyl, or $(C_4-C_8)$-cycloalkyl, R(3) is hydrogen, $(C_1-C_{10})$-alkyl, straight-chain or branched, $(C_3-C_{10})$-alkenyl, straight-chain or branched, phenyl-$(C_1-C_4)$-alkyl, the phenyl group being unsubstituted or substituted by one, two or three substituents from the group consisting of $(C_1-C_4)$-alkyl, $(C_1-C_3)$-alkoxy, halogen, $(C_1-C_2)$-alkylenedioxy and nitro; $(C_4-C_8)$-cycloalkyl, or $(C_4-C_8)$-cycloalkyl-$(C_1-C_4)$-alkyl, R(4) and R(4)' are identical or different and, independently of one another, are hydrogen, $(C_1-C_4)$-alkyl, $(C_1-C_3)$-alkoxy, halogen, nitro, hydroxyl, acetamido or amino, R(5) is hydrogen or $(C_1-C_3)$-alkyl, R(6) is one of the following groups,

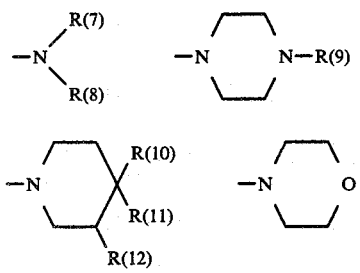

in which

R(7) and R(8) are identical or different and, independently of one another, are hydrogen, $(C_1-C_{10})$-alkyl, $(C_4-C_8)$-cycloalkyl, $(C_4-C_8)$-cycloalkyl-$(C_1-C_4)$-alkyl, phenyl-$(C_1-C_6)$-alkyl, the phenyl radical being unsubstituted or substituted by one, two or three radicals from the group consisting of $(C_1-C_4)$-alkyl, $(C_1-C_4)$-alkoxy, $(C_1-C_2)$-alkylenedioxy, halogen and hydroxyl; or pyridyl-$(C_1-C_4)$-alkyl, R(9) is hydrogen, $(C_1-C_{10})$-alkyl, straight-chain or branched, phenyl, phenyl-$(C_1-C_4)$-alkanoyl or benzoyl, the phenyl radical in each case being unsubstituted or substituted by one, two or three radicals from the group consisting of $(C_1-C_4)$-alkyl, $(C_1-C_4)$-alkoxy, $(C_1-C_2)$-alkylenedioxy, halogen and hydroxyl; pyridyl, pyrimidyl, $(C_1-C_5)$-alkanoyl, R(10) is hydrogen, $(C_1-C_{10})$-alkyl, phenyl, phenyl-$(C_1-C_4)$-alkyl, the phenyl radical in each case being unsubstituted or substituted by one, two or three radicals from the group consisting of $(C_1-C_4)$-alkyl, $(C_1-C_4)$-alkoxy, $(C_1-C_2)$-alkylenedioxy, halogen and hydroxyl:

R(11) is hydrogen, hydroxyl, $(C_1-C_4)$-alkoxy or, together with R(12), is a bond, and R(12) is hydrogen or, together with R(11), is a bond; in which formula I in addition m is 1, 2, 3 or 4, n is 0 or 1, p is 0, 1, 2, 3 or 4, and X is oxygen or two hydrogen atoms, and the salts of the compound of the formula I with physiologically tolerated acids.

2. A compound of the formula I as claimed in claim 1, wherein

R(1) and R(1)' are identical or different and, independently of one another, are hydrogen, methyl, ethyl, methoxy, ethoxy, chlorine, bromine, nitro or acetamide, R(1)'' is hydrogen, R(2) is hydrogen, $(C_1-C_6)$-alkyl, straight-chain or branched, benzyl, phenethyl, allyl, phenyl, 4-methoxyphenyl, 3-methoxyphenyl, 3,4-methylenedioxyphenyl, 3,4,5-trimethoxyphenyl, 3,4-dimethoxyphenyl, cyclohexylmethyl, cyclopentyl, cyclohexyl, cycloheptyl, 4-methoxybenzyl, 3,4-dimethoxybenzyl, 3,4,5-trimethoxybenzyl or 3,4-methylendioxybenzyl, R(3) is hydrogen, $(C_1-C_6)$-alkyl, straight-chain or branched, benzyl, phenylethyl, allyl, cyclopentyl or cyclohexyl, R(4)' is hydrogen, methyl, methoxy, ethoxy, chlorine, nitro, hydroxyl, acetamido or amino, R(4)' is hydrogen, R(5) is hydrogen or methyl, R(6) is one of the following groups,

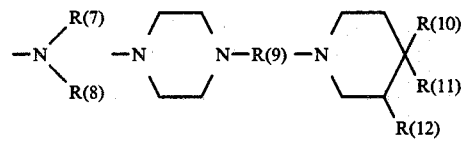

in which

R(7) is hydrogen, methyl, ethyl, propyl or isopropyl,

R(8) is hydrogen, methyl, ethyl, propyl, isopropyl, cyclopentylethyl, cyclohexylethyl, phenyl-$(C_1-C_4)$-alkyl, the phenyl group being unsubstituted or substituted by one, two or three radicals from the group consisting of $(C_1-C_4)$-alkyl, $(C_1-C_4)$-alkoxy, $(C_1-C_2)$-alkylenedioxy, halogen and hydroxyl; or pyridyl-$(C_1-C_4)$-alkyl, R(10) is phenyl or phenyl-$(C_1-C_4)$-alkyl the phenyl group in each case being unsubstituted or substituted by one, two or three radicals from the group consisting of $(C_1-C_4)$-alkyl, $(C_1-C_4)$-alkoxy, $(C_1-C_2)$-alkylenedioxy, halogen and hydroxyl;

R(11) is hydrogen and hydroxyl, methoxy or, together with R(12), is a bond,

R(12) is hydrogen or, together with R(11), is a bond; in which formula I in addition m is 1, 2 or 3, n is 0 or 1, is 1, 2 or 3, and X is oxygen or two hydrogen atoms, and the salts of this compound of the formula I with physiologically tolerated acids.

3. A compound of the formula I as claimed in claim 2, wherein

R(1) is hydrogen, methyl, methoxy, fluorine or chlorine,

R(1)' and R(1)'' are hydrogen,

R(2) is hydrogen, methyl, ethyl, propyl, isopropyl, butyl, sec.-butyl, isobutyl, benzyl, phenethyl, 4-methoxyphenyl, 3-methoxyphenyl, 3,4-dimethoxyphenyl, 3,4,5-trimethoxyphenyl, cyclohexylmethyl, cyclopentyl, cyclohexyl, cycloheptyl, 4-methoxybenzyl, 3,4-dimethoxybenzyl, 3,4,5-trimethoxybenzyl or 3,4-methylenedioxybenzyl, R(3) is hydrogen, methyl, ethyl, propyl, isopropyl, butyl, sec.-butyl, isobutyl, benzyl, phenylethyl, allyl, cyclopentyl or cyclohexyl, R(4) is hydrogen, methoxy, methyl, chlorine, nitro or hydroxyl, R(4)' is hydrogen, R(5) is hydrogen, R(6) is one of the following groups

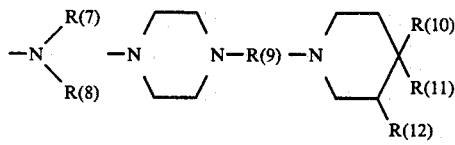

in which

R(7) is hydrogen or methyl,

R(8) is phenyl-$(C_1-C_4)$-alkyl, the phenyl group being unsubstituted or substituted by one, two or three radicals from the group consisting of methyl, methoxy, chlorine, methylenedioxy and hydroxyl;

R(10) is phenyl, the phenyl group being unsubstituted or substituted by one, two or three radicals of the group consisting of methyl, methoxy, chlorine, methylenedioxy and hydroxyl, R(11) is hydrogen, hydroxyl, methoxy or, together with R(12), is a bond, and R(12) is hydrogen or, together with R(11), is a bond;

in which formula I in addition m is 1, 2 or 3, n is 0, is 0, 1 or 2, and

X is oxygen, and the salts of this compound of the formula I with physiologically tolerated acids.

4. A compound of the formula I as claimed in claim 3, wherein

R(2) is hydrogen, methyl, ethyl, propyl, isopropyl or phenyl,

R(3) is methyl, ethyl, propyl, isopropyl, butyl, sec.-butyl, isobutyl, cyclopentyl or cyclohexyl, R(4) is hydrogen, methoxy, methyl or chlorine, R(6) is one of the following groups

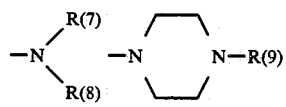

in which

R(7) is methyl,

R(9) is phenyl-$(C_1-C_4)$-alkyl, the phenyl group being unsubstituted or substituted by one, two or three radicals from the group consisting of $(C_1-C_2)$-alkoxy, $(C_1-C_2)$-alkylenedioxy and hydroxyl, m is 3, p is 0 or 1, and the salts of this compound with physiologically tolerated acids.

5. A compound of the formula I as claimed in claim 4, wherein

R(1) is hydrogen,

R(2) is methyl,

R(3) is methyl, ethyl, isopropyl, isobutyl, sec.-butyl or cyclopentyl,

R(6) is

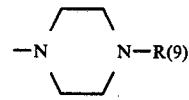

and

R(9) is phenyl-$(C_1-C_3)$-alkyl, the phenyl group being unsubstituted or substituted by one, two or three methoxy groups, and its physiologically tolerated salts.

6. A compound as claimed in claim 1 which is 2,3-dihydro-2,4-dimethyl-2-[2-[4-[4-[2-(3,4,5-trimethoxyphenyl)ethyl]piperazinyl]butoxy]phenyl]-1,4-benzothiazin-3-one and its physiologically tolerated salts.

7. A compound as claimed in claim 1 which is 2,3-dihydro-2-ethyl-4-methyl-2-[2-[4-[4-[2-(3,4,5-trimethoxyphenyl)ethyl]piperazinyl]butoxy]phenyl]-1,4-benzothiazin-3-one and its physiologically tolerated salts.

8. A compound as claimed in claim 1, which is 2,3-dihydro-2-isopropyl-4-methyl-2-[2-[4-[4-[2-(3,4,5-trimethoxyphenyl)ethyl]piperazinyl]butoxy]phenyl]-1,4-benzothiazin-3-one and its physiologically tolerated salts.

9. A compound as claimed in claim 1, which is (+)-2,3-dihydro-2-isopropyl-4-methyl-2-[2-[4-[4-[2-(3,4,5-trimethoxyphenyl)ethyl]piperazinyl]butoxy]phenyl]-1,4-benzothiazin-3-one and its physiologically tolerated salts.

10. A compound of the formula II

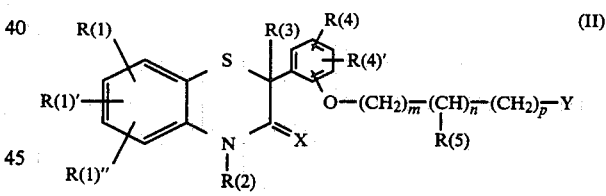

in which R(1), R(1)', R(1)", R(2), R(3), R(4), R(4)', R(5), X, m, n and p have the same meaning as in claim 1, and in which Y is a halogen atom, a methanesulfonyl radical, a benzenesulfonyl radical, a toluenesulfonyl radical or a trifluoromethanesulfonyl radical.

11. A medicament for diminuishing the influx of calcium ions into cells which contains or is composed of a compound of the formula I as claimed in claim 1 or a salt of this compound with a physiologically tolerated acid.

12. Method for the treatment of disturbances of the calcium balance of a human or animal body which comprises administering a compound of the formula I as claimed in claim 1 or one of its salts with a physiologically tolerated salt in an effective amount.

* * * * *